US012699100B2

(12) United States Patent
Lu et al.

(10) Patent No.: US 12,699,100 B2
(45) Date of Patent: Aug. 4, 2026

(54) DEEP LEARNING SYSTEM FOR PREDICTING THE T CELL RECEPTOR BINDING SPECIFICITY OF NEOANTIGENS

(71) Applicant: THE BOARD OF REGENTS OF THE UNIVERSITY OF TEXAS SYSTEM, Austin, TX (US)

(72) Inventors: Tianshi Lu, Dallas, TX (US); Tao Wang, Coppel, TX (US)

(73) Assignee: THE BOARD OF REGENTS OF THE UNIVERSITY OF TEXAS SYSTEM, Austin, TX (US)

( * ) Notice: Subject to any disclaimer, the term of this patent is extended or adjusted under 35 U.S.C. 154(b) by 797 days.

(21) Appl. No.: 18/029,395

(22) PCT Filed: Sep. 30, 2021

(86) PCT No.: PCT/US2021/053006
§ 371 (c)(1),
(2) Date: Mar. 30, 2023

(87) PCT Pub. No.: WO2022/072722
PCT Pub. Date: Apr. 7, 2022

(65) Prior Publication Data
US 2023/0349914 A1 Nov. 2, 2023

Related U.S. Application Data

(60) Provisional application No. 63/085,911, filed on Sep. 30, 2020.

(51) Int. Cl.
| | |
|---|---|
| *G06N 3/08* | (2023.01) |
| *G01N 33/68* | (2006.01) |
| *G06N 3/0455* | (2023.01) |
| *G16B 15/30* | (2019.01) |
| *G16B 40/20* | (2019.01) |

(52) U.S. Cl.
CPC ....... *G01N 33/6845* (2013.01); *G06N 3/0455* (2023.01); *G06N 3/08* (2013.01); *G16B 15/30* (2019.02); *G16B 40/20* (2019.02)

(58) Field of Classification Search
None
See application file for complete search history.

(56) References Cited

FOREIGN PATENT DOCUMENTS

WO 2019075112 A1 4/2019

OTHER PUBLICATIONS

Springer et al. "Prediction of Specific TCR-Peptide Binding From Large Dictionaries of ICR-Peptide Pairs" 1-10. Frontiers In Immunology vat 11, Article 1803. Online. Aug. 25, 2020; [retrieved Dec. 29, 2021]. Retrieved from the Internet: <URL: https://www.frontiersin. orgfarticles/10.3389/fimmu.2020.01803/full>: DOI: 10.3389/fimmu. 2020.01803.

Carbone et al. in vitro reconstitution of T cell receptor-mediated segregation of the CD45 phosphatase pp. E3938-E3945. PNAS.org. Online. Oct. 17, 2017; [retrieved Jan. 3, 2021]. Retrieved from the Internet: <URL: https://www.pnas.orgicontent/pnes/114/44/E9338. full.pdf>.

Cai et al. "TCR-epitope binding affinity prediction using multi-head self attention model" pp. 1.5. ICML Workshop on Computational Biology. Online. Jul. 25, 2021; Publication [online]. Jul. 25, 2021 [retrieved Dec. 29, 2021]. Retrieved from the Internet: <URL: https://icml-comphio.github.lo/2021/papers/WCBICML2021_paper_ 59.pdf.

International Search Report and Written Opinion of the International Searching Authority issued in International Application No. PCT/US2021/053006, 5 pages, dated Feb. 3, 2022.

Liu, Y. C. et al. Highly divergent T-cell receptor binding modes underlie specific recognition of a bulged viral peptide bound to a human leukocyte antigen class I molecule. I Biol. Chem. 288, 15442-15454 (2013).

Cole, D. K. et al. T-cell receptor (TCR)-peptide specificity overrides affinity-enhancing TCR-major histocompatibility complex interactions. J. Biol. Chem. 289, 628-638 (2014).

Valkenburg, S. A. et al. Molecular basis for universal HLA-A*0201-restricted CD8+ T-cell immunity against influenza viruses. Proc Nall Acad Sci USA 113, 4440-4445 (2016).

Cherkasova, E. et al. Detection of an Immunogenic HERV-E Envelope with Selective Expression in Clear Cell Kidney Cancer. Cancer Res. 76, 2177-2185 (2016).

Liu, D. et al. Integrative molecular and clinical modeling of clinical outcomes to PD1 blockade in patients with metastatic melanoma. Nat. Med. 25, 1916-1927 (2019).

Van Allen, E. M. et al. Genomic correlates of response to CTLA-4 blockade in metastatic melanoma. Science 350, 207-211 (2015).

(Continued)

*Primary Examiner* — Christopher M Gross
(74) *Attorney, Agent, or Firm* — DLA Piper LLP US

(57) ABSTRACT

Neoantigens play a key role in the recognition of tumor cells by T cells. However, only a small proportion of neoantigens truly elicit T cell responses, and fewer clues exist as to which neoantigens are recognized by which T cell receptors (TCRs). To help determine the TCRs that interact with particular neoantigens, prediction models that predict TCR-binding specificities of neoantigens presented by different classes of major histocompatibility complex (MHCs) were developed. To confirm the applicability of the model to clinical settings, the prediction models were comprehensively validated by a series of analyses. The validated prediction models used a flexible transfer learning approach and differential learning schema to achieve highly accurate prediction of TCR binding specificity only using TCR sequence data, antigen sequence data, and MHC alleles.

20 Claims, 31 Drawing Sheets

(56) References Cited

OTHER PUBLICATIONS

Hugo, W. et al. Genomic and Transcriptomic Features of Response
to Anti-PD-1 Therapy in Metastatic Melanoma. Cell 165, 35-44
(2016).
Miao, D. et al. Genomic correlates of response to immune check-
point therapies in clear cell renal cell carcinoma. Science 359,
801-806 (2018).

Original CDR3s (Amino acids)

Original CDR3s (Atchley factors)

Reconstructed CDR3s (Atchley factors)

CASSEGTGGADTQYFGPG

CASSLWGTDNEQYFGPG

Cellular Response to IL7
Cytokine-mediated pathway
DC Antigen Processing and Presentation
Regulation of Immune System
Response to IL7
T cell Migration

| Cohort | Binding Rank Cutoff | Binding Rank P Value | P Value (Neoantigen Load) | P Value (T Cell Infiltration) | P Value (TCR Diversity) |
|---|---|---|---|---|---|
| LUAD | 0.01% | 0.017 | 0.963 | 0.55 | 0.350 |
| | 0.05% | 0.002 | | | |
| | 0.2% | 0.006 | | | |
| LUSC | 0.01% | 0.006 | 0.421 | 0.201 | 0.215 |
| | 0.05% | 0.100 | | | |
| | 0.2% | 0.028 | | | |
| SKCM | 0.01% | 0.025 | 0.212 | 0.223 | 0.709 |
| | 0.05% | 0.005 | | | |
| | 0.2% | 0.0004 | | | |
| RCC | 0.01% | 0.332 | 0.289 | 0.260 | 0.196 |
| | 0.05% | 0.339 | | | |
| | 0.2% | 0.038 | | | |

FIG. 30

DEEP LEARNING SYSTEM FOR PREDICTING THE T CELL RECEPTOR BINDING SPECIFICITY OF NEOANTIGENS

CROSS REFERENCE TO RELATED APPLICATIONS

This application is a U.S. National Stage Application of International Application No. PCT/US2021/053006, filed Sep. 30, 2021, which claims priority pursuant to 35 USC § 119(e) to U.S. provisional patent application No. 63/085,911 filed Sep. 30, 2020. Each of the foregoing are hereby incorporated herein by reference in their entireties.

STATEMENT REGARDING FEDERALLY SPONSORED RESEARCH OR DEVELOPMENT

This invention was made with government support under grant number CA258584 awarded by The National Institutes of Health and grant number RP190208 awarded by Cancer Prevention and Research Institute of Texas. The government has certain rights in the invention.

BACKGROUND

Neoantigens are short peptides presented by major histocompatibility complex (MHC) proteins on the surface of tumor cells, which are transcribed and translated from somatically mutated genes in the tumors. Neoantigens serve as recognition markers for cytotoxic T cells via their interactions with T cell receptors (TCRs) and are a key player in the process of immunoediting. Immunotherapies, while having transformed cancer patient care, benefit only a small subset of patients. Neoantigens have been increasingly shown to be the targets of checkpoint inhibitor-induced immune responses. Therefore, an accurate and comprehensive characterization of the interactions between neoantigens and the immune system is central for understanding cancer progression, prognosis, and responsiveness to immunotherapy.

One of the most fundamental and unsolved questions regarding neoantigens and antigen biology in general is the lack of understanding of why not all neoantigens are immunogenic (i.e., attract T cells or provoke another immune response). Moreover, we know even less about the T-cell receptor (TCR) binding specificity of immunogenomic neoantigens, which are presented by a certain class of MHC proteins (pMHCs). The ability to link pMHCs to TCR sequences is essential for monitoring the interactions between the immune system and tumors. Additional insights into the interactions between pMHCs and TCR sequences could be used to enhance the design or implementation of various types of immunotherapies. For example, the selection of candidates for synthesizing neoantigen vaccines could be informed by whether there are any existing pairing detected between the antigen candidates and the patient's TCR repertoire.

Existing approaches to detecting TCR and pMHC pairs (e.g., tetramer analysis, TetTCR-seq, and T-scan) are time-consuming, technically challenging, and too costly to be clinically viable. Additionally, these approaches are experimental and have not been rigorously validated or even validated at all in clinical settings. Therefore, there exists a well-established need for developing machine learning approaches to predict TCR binding specificity of neoantigens. Data driven approaches to identifying TCR and pMHC pairs would significantly reduce the time and cost of identifying the pairings and can complement experimental approaches by streamlining the validation of existing techniques and facilitating the development of improved experimental approaches.

SUMMARY

In this work, transfer learning, a newer branch of deep learning, was used to train one or more models that can predict the TCR binding specificity of classes of pMHCs. The trained models were systematically validated using several independent validation datasets and demonstrated the advance of the models over previous works. The trained models were also applied to human tumor sequencing data to generate novel insights regarding the sources of immunogenicity, prognosis and treatment response to immunotherapies. Overall, the models for predicting TCR binding addressed the long-standing TCR-pMHC pairing prediction problem, revealed biological insights on the genome-wide scale, and demonstrated efficacy as a basis for constructing biomarkers for predicting immunotherapy response.

Disclosed herein are methods of predicting T cell receptor (TCR) binding specificities comprising: determining a set of MHC embeddings that encode neoantigen and major histocompatibility complex (MHC) data for a plurality of MHC proteins (pMHC); determining a set of TCR embeddings that encode TCR data for a plurality of TCR sequences; pre-training a prediction model on the set of MHC embeddings and the set of TCR embeddings; training the prediction model using a differential learning schema that feeds a binding TCR-pMHC pair and a non-binding TCR-pMHC pair into the prediction model during each training cycle; and determining a prediction for binding specificity of an input TCR-pMHC pair based on the prediction model.

The disclosed methods may further comprise obtaining a set of TCR-pMHC pairs that are experimentally validated as immunogenic, the set of TCR-pMHC pairs including the input TCR-pMHC pair; and validating the prediction model by comparing the binding specificity prediction for the input TCR-pMHC pair to a known binding specificity for the input TCR-pMHC pair. The disclosed methods may further comprise determining a clonal expansion of a plurality of T cells, the clonal expansion including multiple TCR clones having known binding interactions with a set of pMHCs and a clone size for each of the multiple TCR clones; determining a prediction for binding specificity between each of the multiple TCR clones and each of the pMHCs included in the set of pMHCs based on the prediction model; and validating the prediction model by comparing the clone size for each of the TCR clones to the predicted binding specificity.

In various embodiments each of the MEW embeddings may include a numeric representation of one or more pMHCs. The disclosed methods may further comprise training a MEW numeric embedding layer on a MHC training dataset including textual representations of pMHCs; and determining the numeric representation of the one or more pMHCs for each of the MEW embeddings based on the MHC numeric embedding layer.

In various embodiments, the MHC embeddings may be determined using a multi-layer neural network that determines a probability that a particular pMHC molecule binds to one or more neo-antigen protein sequences. In various embodiments, each of the TCR embeddings may include a numeric representation of one or more TCR protein sequences.

The disclosed methods may further comprise training a TCR numeric embedding layer on a TCR training dataset including multiple training TCR protein sequences, the TCR training dataset including a structured data representation of one or more biochemical properties of multiple amino acids included in the training TCR protein sequences; and determining the numeric representation of the one or more TCR protein sequences based on the TCR numeric embedding layer.

In various embodiments, the multiple amino acids may be included in a complementary determining region (CDR) of the training TCR protein sequences. The disclosed methods may further comprise manipulating the structured data representation to enable amino acids from multiple CDRs of the training TCR protein sequences to be added to the TCR training dataset. In various embodiments, the TCR embeddings may be determined using an auto-encoder that includes multiple encoder layers and multiple decoder layers.

The disclosed methods may further comprise normalizing the MHC embeddings and the TCR embeddings to enable the prediction model to be pre-trained on multiple classes of pMHCs In various embodiments, the prediction for binding specificity includes a variable that describes a percentile rank of a predicted binding strength between the input TCR-pMHC pair, with respect to a pool of 10,000 randomly sampled TCRs (as a background distribution) against the pMHC included in the TCR-pMHC pair.

Disclosed herein are systems for predicting T cell receptor (TCR) binding specificities comprising: a memory including executable instructions; and a processor that may be configured to execute the executable instructions and cause the system to: determine a set of MHC embeddings that encode neoantigen and major histocompatibility complex (MHC) data for a plurality of MHC proteins (pMHC); determine a set of TCR embeddings that encode TCR data for a plurality of TCR sequences; pre-train a prediction model on the set of MHC embeddings and the set of TCR embeddings; train the prediction model using a differential learning schema that feeds a binding TCR-pMHC pair and a non-binding TCR-pMHC pair into the prediction model during each training cycle; and determine a prediction for binding specificity of an input TCR-pMHC pair based on the prediction model.

In various embodiments, the processor may be further configured to: obtain a set of TCR-pMHC pairs that are experimentally validated as immunogenic, the set of TCR-pMHC pairs including the input TCR-pMHC pair; and validate the prediction model by comparing the binding specificity prediction for the input TCR-pMHC pair to a known binding specificity for the input TCR-pMHC pair. In various embodiments, the processor may be further configured to: determine a clonal expansion of a plurality of T cells, the clonal expansion including multiple TCR clones having known binding interactions with a set of pMHCs and a clone size for each of the multiple TCR clones; determine a prediction for binding specificity between each of the multiple TCR clones and each of the pMHCs included in the set of pMHCs based on the prediction model; and validate the prediction model by comparing the clone size for each of the TCR clones to the predicted binding specificity.

In various embodiments, each of the MHC embeddings may include a numeric representation of one or more pMHCs, and the processor may be further configured to: train a MHC numeric embedding layer on a MHC training dataset including textual representations of pMHCs; and determine the numeric representation of the one or more pMHCs for each of the MHC embeddings based on the MHC numeric embedding layer. In various embodiments, the MHC embeddings may be determined using a multi-layer neural network that determines a probability that a particular pMHC molecule binds to one or more neo-antigen protein sequences.

In various embodiments, each of the TCR embeddings may include a numeric representation of one or more TCR protein sequences, and the processor may further be configured to: train a TCR numeric embedding layer on a TCR training dataset including multiple training TCR protein sequences, the TCR training dataset including a structured data representation of one or more biochemical properties of multiple amino acids included in the training TCR protein sequences; and determine the numeric representation of the one or more TCR protein sequences based on the TCR numeric embedding layer.

In various embodiments, the multiple amino acids may be included in a complementary determining region (CDR) of the training TCR protein sequences, and the processor may be further configured to: manipulate the structured data representation to enable amino acids from multiple CDRs of the training TCR protein sequences to be added to the TCR training dataset. In various embodiments, the TCR embeddings may be determined using an auto-encoder that includes multiple encoder layers and multiple decoder layers.

In various embodiments, the processor may be further configured to normalize the MHC embeddings and the TCR embeddings to enable the prediction model to be pre-trained on multiple classes of pMHC. In various embodiments, the prediction for binding specificity may include a variable that describes a percentile rank of a predicted binding strength between the input TCR-pMHC pair, with respect to a pool of 10,000 randomly sampled TCRs (as a background distribution) against the pMHC included in the TCR-pMHC pair.

BRIEF DESCRIPTION OF THE DRAWINGS

The accompanying drawings are included to provide a further understanding of the methods and compositions of the disclosure, are incorporated in, and constitute a part of this specification. The drawings illustrate one or more embodiments of the disclosure, and together with the description serve to explain the concepts and operation of the disclosure.

FIG. 30 is a table illustrating the results of an analysis of other candidate biomarkers performed on the lung cancer and melanoma cohorts, according to various embodiments of the present disclosure.

DETAILED DESCRIPTION

Disclosed herein are machine learning systems and methods for predicting the TCR binding specificity of classes of pMHCs. The machine learning models generated by the system are validated using several independent validation datasets. The machine learning models predicted the TCR-binding specificity of classes of pMHCs, given only the TCR sequence, (neo)antigen sequence, and MHC type, which has never been done before. Generating accurate predictions from this reduced dataset is possible by several innovative algorithmic designs, including transfer learning techniques which leverage of a large amount of related TCR and pMHC data that do not have any pairing labels. The machine learning models were also trained using a differential training paradigm that allows the models to focus on differentiating binding vs. non-binding TCRs (i.e., learn the characteristics of TCRs and pMHC that are indicative of binding) instead of memorizing the pairing relationships included a training dataset. The machine learning models were used to analyze human tumor sequencing data in order to make predictions regarding the sources of immunogenicity, prognosis and treatment response to immunotherapies. This technology addresses the long-standing TCR-pMHC pairing prediction problem, reveals unique biological insights on a genome-wide scale, and serves as a basis for constructing biomarkers for predicting immunotherapy response.

Figure 1:
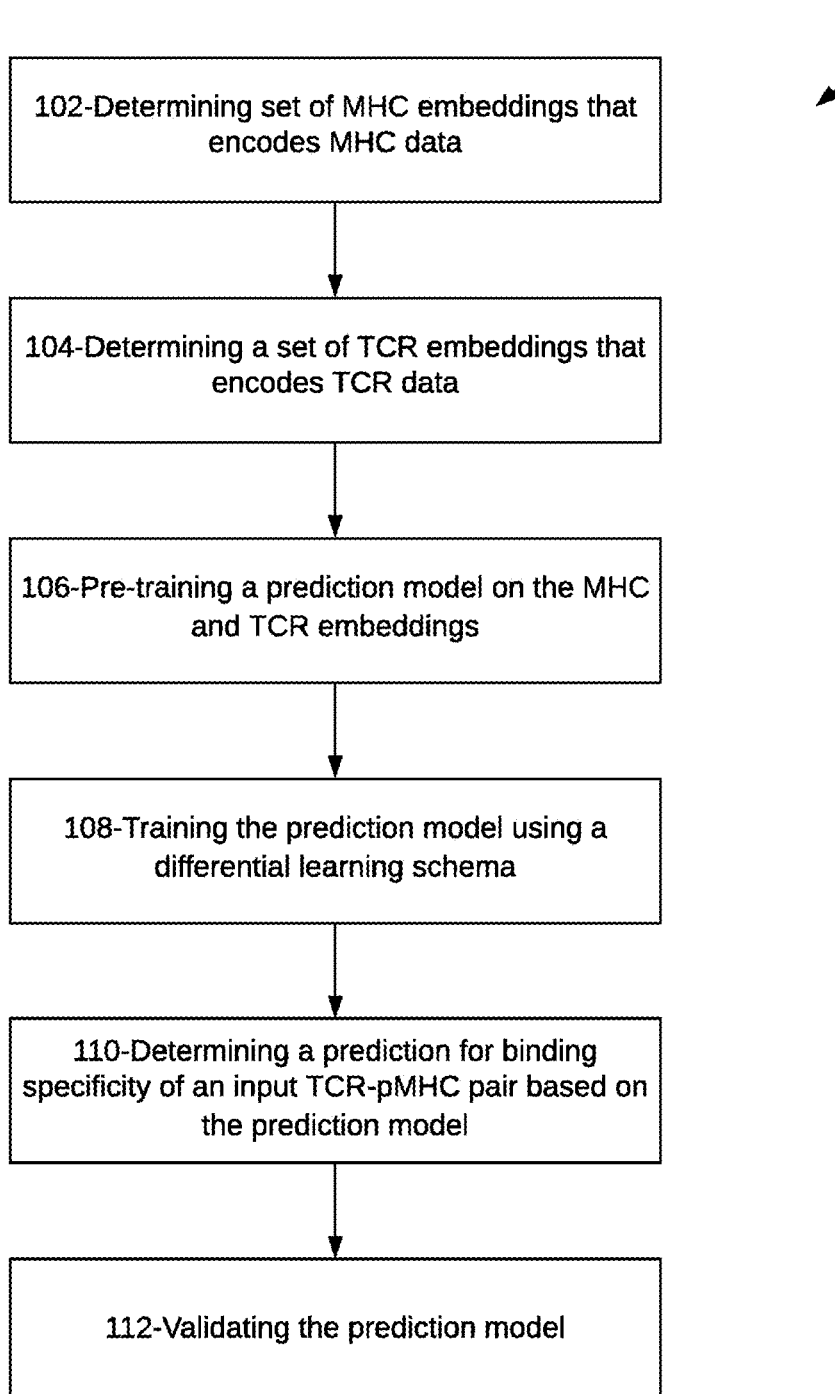
FIG. 1 illustrates an exemplary process for training a machine learning model to predict TCR binding specificities, according to various embodiments of the disclosure.

FIG. 1 is a block diagram illustrating an example process 100 for training a machine learning model to predict TCR binding specificities. At step 102, a set of MHC embeddings is determined. The MHC embeddings may encode neoantigen and MHC data for a plurality of pMHCs. Each of the MHC embeddings may include a numeric representation of one or more pMHCs generated by a multi-layer neural network or other MHC numeric embedding layer. For example, to generate the MHC embeddings, the MHC numeric embedding layer may be trained on a MHC training dataset including textual representations of pMHCs. The MHC numeric embedding layer may convert the sequence data for a group of input MHC sequences into numeric feature vectors by performing a prediction task that predicts the probability neo-antigen sequences will bind to a particular pMHC.

At step 104, a set of TCR embeddings is determined. The TCR embeddings may include a numeric representation of TCR sequences generated by an auto-encoder or other TCR numeric embedding layer. For example, the TCR numeric embedding layer may be trained on a TCR training dataset that includes multiple training TCR sequences. The TCR training dataset may include TCR data, for example, a matrix or other structured data representation of one or more biochemical properties of amino acids included in each of the training TCR protein sequences. The auto-encoder or other TCR numeric embedding layer may include a plurality of encoder layers that encode the structured data representations into feature vectors. The auto-encoder may also include a plurality of decoder layers that generate a reconstruction of the structured data representations based on the feature vectors generated by the encoder layers. Accordingly, the TCR embeddings may be validated by comparing the structured data representations input into the encoder layers to the reconstruction of the structured data representations generated by the decoder layers. A high degree of similarity (i.e., % similar or any other measure of similarity that is at or above a pre-defined similarity threshold) between the input structured data representations and the reconstruction may indicate accurate TCR embeddings.

The structured data representation may also be manipulated to enable biochemical properties of other portions of the training TCR sequences (e.g., amino acids from CDR-1, CDR-2, and other completer determining regions) to be incorporated into the TCR training data. For example, the matrices including Atchley factors or other the representations of properties of TCR sequences may be padded (i.e., expanded to include unfilled columns/rows of data) to leave space for additional properties of the TCR sequences. The TCR embeddings may be retrained using updated data structured data representations that include additional properties to improve the accuracy of the TCR embeddings.

At step 106, a prediction model is pre-trained on the MHC and TCR embeddings. For example, one or more pre-training layers included in the prediction model may be trained to generate numeric vector encodings of input TCRs and pMHCs based on the MHC and TCR embeddings. At step 108, the prediction model is trained using a differential learning schema. The differential learning schema may feed a binding TCR-pMHC pair and a non-binding TCR-pMHC pair into the prediction model during each training cycle in order to get the prediction model to recognize characteristics of binding and non-binding TCRs and pMHCs instead of memorizing the binding pairings included in the training dataset. At step 110, the prediction model determines a prediction for a binding specificity of an input TCR-pMHC pair.

At step 112, the prediction model may be validated. For example, the prediction model may be validated by comparing binding specificity predictions to known binding interactions. To validate the prediction model based on known binding interactions, a set of TCR-pMHC pairs that includes the input TCR-pMHC pair may be obtained. Each of the TCR-pMHC pairs included in the set may be experimentally validated as immunogenic and may have a previously known binding specificity (i.e., a binding specificity reported in a publication or obtained experimentally). The predicated binding specificity generated by the prediction model may then be compared to the previously known binding specificity for the input TCR-pMHC pair to validate the prediction model. A high degree of similarity between the predicted bindings specificities and the previously known binding specificities may indicate high performing (i.e., accurate) prediction models.

The prediction model may also be validated based on the relationship between predicted binding strength and clonal expansion of T cells. For example, a clonal expansion of a plurality of T cells may be determined. The clonal expansion may include multiple TCR clones having known binding interactions with a set of pMHCs and a clone size for each of the multiple TCR clones. The machine learning model may then generate a prediction for binding specificity between each of the multiple TCR clones and each of the pMHCs included in the set of pMHCs. The prediction model may then be validated by comparing the clone size for each of the TCR clones to the predicted binding specificity. An inverse relationship between clone size and binding specificity (e.g., small clone sizes and high binding specificity rank) may indicate high performing (i.e., accurate) predictions models.

The binding specificity predictions generated by the validated prediction model may be used in many clinical applications. For example, the binding specificity predictions may be used to select the most effective TCR for TCR-T therapies. To determine the TCR with the highest potential efficacy in a TCR-T treatment, a pMHC may be obtained from a patient sample. The prediction model may then predict the TCR from the available TCR-T treatments that has the strongest binding specificity for the patient's pMHC, with the TCR having the strongest predicted binding specificity selected for use during the treatment. The prediction model may also be used to select neoantigens for neoantigen vaccine therapies. For example, the prediction model could predict the TCRs that would be most effective at targeting specific tumors allowing for preparation of a vaccine including neoantigens that can activate the targeted T cells with these TCRs. The binding specificity predictions generated by the prediction model can also be used as a genomics-based biomarker for predicting patient specific treatment responses. For example, patient responses to tumor immune checkpoint inhibitors.

Model Architecture—Deep Learning the TCR-Binding Specificity of Neoantigens

Figure 2:
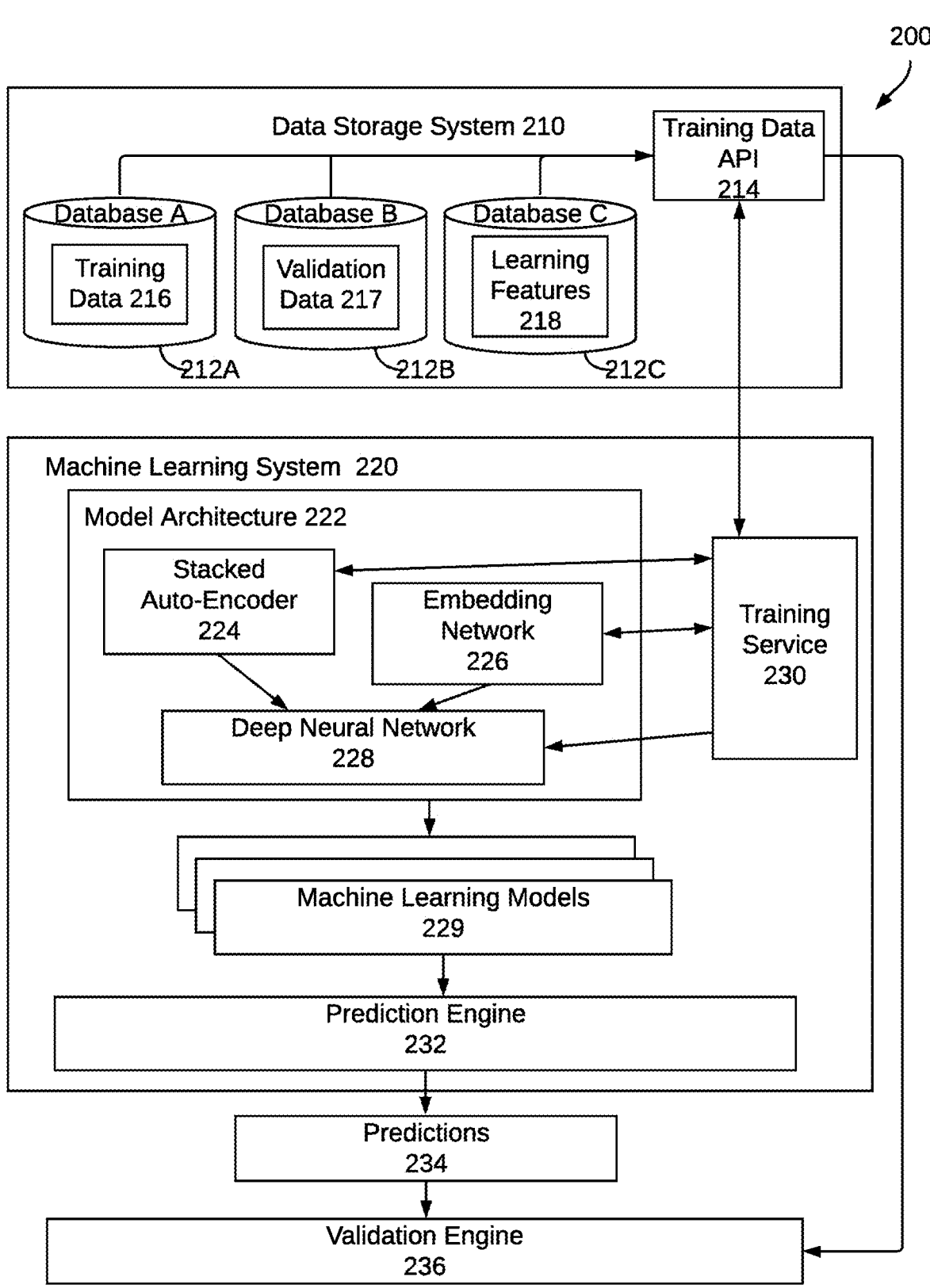
FIG. 2 illustrates an exemplary machine learning system used to implement the process shown in FIG. 1, according to various embodiments of the disclosure.

FIG. 2 is a block diagram illustrating an exemplary system 200 for generating and validating machine learning models 229 that predict TCR binding specificity of neoantigens (pMHCs). A training service 230 generates the machine learning models 229 using a model architecture 222 that implements a staged three step training process that lowers the difficulty level of the prediction task. The model architecture 222 includes an embedding network 226, a stacked auto-encoder, and a deep neural network 228 that are used to implement the three step training process. To train the machine learning models 229, the training service 230 feeds training data from the data storage system 210 into each component of the model architecture 222. The training service 230 may request specific types of training data for one or more of the components of the model architecture 222 by calling an training data API 214 or otherwise communicating with the data storage system 210.

In various embodiments, to train the machine learning models, the embedding network 226 first determines numeric embeddings of pMHCs that represent the protein sequences of neoantigens and the MHCs numerically. Second, the stacked auto-encoder 224 determines an embedding of TCR sequences that encode text strings of TCR sequences numerically. The two step approach to numerically encoding pMHCs and TCR sequences provides several advantages that improve the computational efficiency of the training process and the flexibility of the trained models. For example, the two step pMHC and TCR encoding process creates numeric vectors that are manageable for mathematical operations and sets the stage for the final pairing prediction. Additionally, the embeddings (feature vectors) generated using this approach are flexible so that TCR CDR3βs, MHC alleles, and peptides that have not been used in the training phase can be processed by the system during the testing phase, as only the sequence information of the (new) TCRs, MHCs, and the peptides are fed into the embeddings. Once the embeddings are generated, a deep neural network 228 (e.g., a fully connected deep neural network) is deployed on top of the two embeddings (to transfer knowledge from them) to form an integrated model architecture. The deep neural network 228 is then fine-tuned to finalize the machine learning models 229 for predicting the pairing between TCRs and pMHCs.

Figure 3:
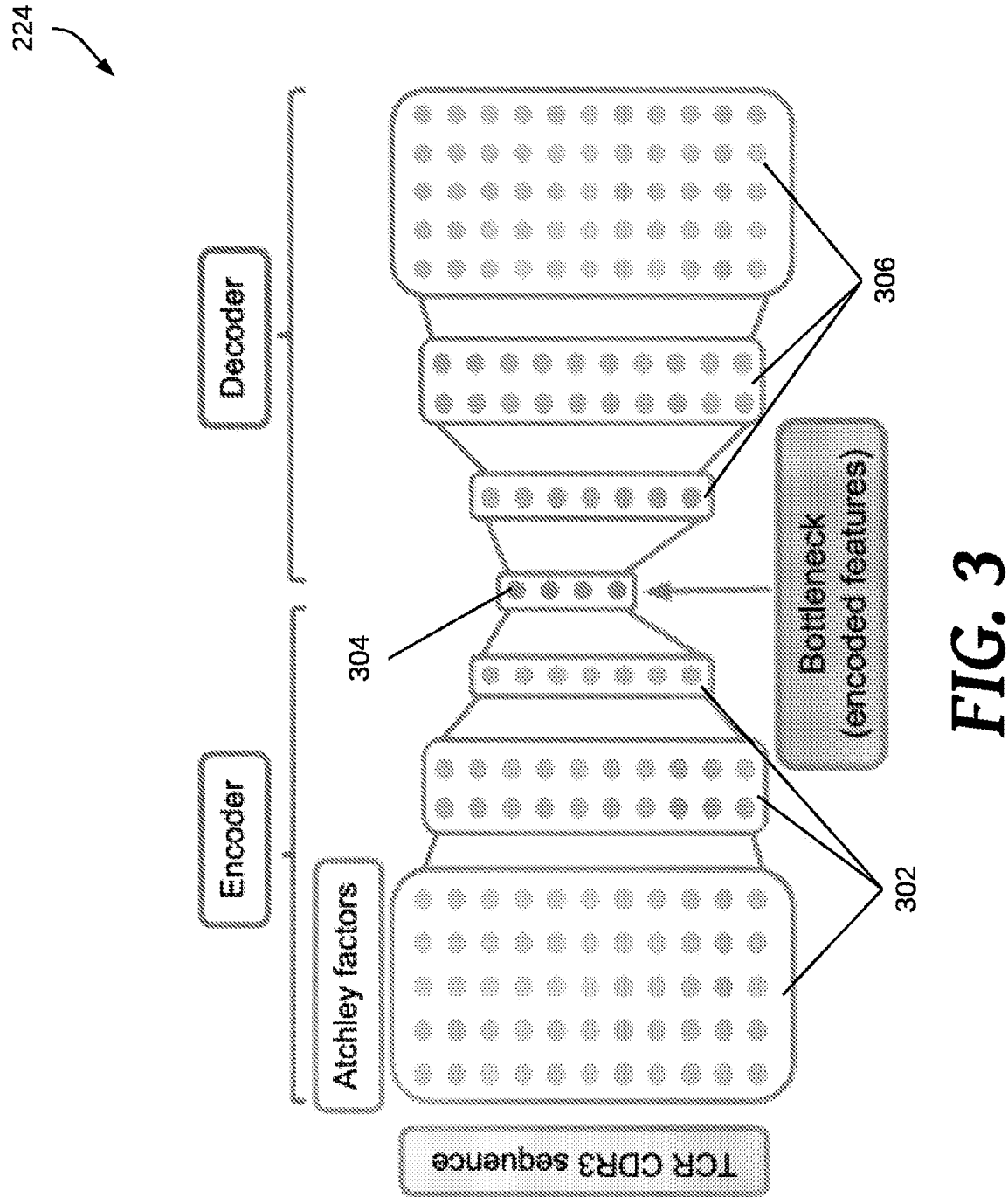
FIG. 3 illustrates an exemplary stacked auto-encoder included in the machine learning system, according to various embodiments of the disclosure.

FIG. 3 illustrates more details of the stacked autoencoder 224 which can capture key features the TCR sequences using an unsupervised decompose-reconstruction process. The stacked auto-encoder 224 may embed the captured features in a short numeric vector that may be used to transfer knowledge of the TCR sequences to a machine learning model that predicts TCR-pMHC binding efficiency. The stacked auto-encoder 224 may include one or more encoder layers 302 that numerically encode the TCR sequences (e.g., TCR CDR3β sequences). The one or more encoder layers 302 may be used to derive features and other numeric signals from the TCR sequences using one or more unsupervised learning algorithms. To encode the TCR sequences, the encoder layers 302 may use the Atchley factors which represent each amino acid included in the TCR sequences with 5 numeric values. These 5 values comprehensively characterize the biochemical properties of each amino acid. The resulting numeric matrix may have a number of rows matching the number of Atchley factors (i.e., 5) and any number of columns (e.g., 80 columns). The "Atchley matrices" of TCR sequences can be fed into the one or more encoder layers 302 to derive the encoded features 304 of the TCR sequences.

The one or more encoder layers 302 may include a one or more convolution layers, normalization layers, pooling layers, dropout layers, dense layers, and the like. For example, the Atchley matrices may be fed into a first convolution layer (e.g., a 2D convolution layer having 30 5×2 kernels). Each kernel in the first convolution layer may extract features from a portion of the Atchley matrices and generate an output. An activation function (e.g., a scaled exponential linear units (SELU) function) included in the first convolutional layer may define the format of the features extracted from the Atchley factors that are included in the output of the first convolution layer. Output from the first convolution layer may then be fed into a first batch normalization layer and a first pooling layer (e.g., a 2D average pooling layer with 4×1 kernels). The first pooling layer may combine the outputs from the first convolution layer to reduce the dimensionality by one (e.g., from 5×1 to 4×1). The first pooling layer may be followed by a second convolutional layer (e.g., a second 2D convolution layer with 20 4×2 kernels). The output from the second convolution layer may be fed into the same batch normalization layer and the same pooling layer as previously described (i.e., the 2D average pooling layer). After pooling, the 4×2 matrices can be converted into a flattened layer. The flattened output may be fed into a dense layer (e.g., a 30-neuron dense layer activated with the SELU activation function), and a dropout layer (e.g., a dropout layer with a dropout rate 0.01). Output from the dropout layer may be fed into a bottleneck layer which generates the learned encoded features 304. The bottleneck layer may be a second 30-neuron dense layer activated with the SELU function.

A decoder including one or more decoder layers 306 may then reconstruct the Atchley matrices for the TCR sequences input into the encoder layers 302. The decoder layers 306 may reverse the outputs of the encoder layers 302 so that the output of the last of the decoder layers 306 (e.g., a decoder layer reversing the operation of the first convolution layer) matches the Atchley matrices that were input into the encoder layers 302. Accordingly, the input of the encoder layers 302 and output of decoder layers 306 can be exactly the same (the Atchley matrices). During the training process, the training tasks performed by the stacked auto-encoder 224 can include reconstructing the input data and capturing the inherent structure of the Atchley factor representations of the TCR sequences using a simple numeric vector. After training is finished, the smallest fully connected layer in the middle of the stacked auto-encoder 224 (i.e., the bottleneck layer) can form a 30 neuron numeric vector embedding of the original CDR3s of the TCR sequences.

The numeric embedding of TCRs learned by the stacked auto-encoder 224 may focus on the CDR3 regions of TCRβ chains, which is the key determinant of specificity in antigen recognition. To allow the system to test a wide variety of TCR sequences and multiple regions of different TCR sequences, the Atchley matrices may be padded to enable each matrix to accept one or more sequences having a total length of at least 80 amino acids. For example, the Atchley matrices may include 30 columns that are filled with TCR CDR3β sequence data. Any number of additional columns may be added to the matrices to allow more sequence data to be incorporated into the TCR embeddings. For example, the Atchley matrices may include 80 columns with 30 of the columns for the TCR CDR3β sequence data and 50 columns of padding. Any number of columns of padding may be added to the Atchley matrices, however, 50 columns was selected for one embodiment of the matrices because it includes enough columns to support sequence data from additional regions and/or chains but also keeps the total number of columns limited to reduce the computational complexity and processing time required determine the TCR embeddings. The padded columns included in the Atchley matrices may incorporate sequence data from other elements of TCRs. For example, the 50 or more padded columns may incorporate sequence data from other regions of the TCR chains (e.g., CDR1 and CDR2). Sequence data from other TCR chains (e.g., TCR a chains) may also be added to the padded columns included in the matrices. The flexible architecture of the Atchley matrices used by stacked auto-encoder 224 allow TCR embeddings to be generated from multiple TCR chains and multiple TCR chain regions without modifying the structure of the stacked auto-encoder 224 in order to accommodate sequence data from a particular CDRs and/or TCR chain. Accordingly, the stacked auto-encoder 224 may be used to generate TCR embeddings from sequence data including any number of amino acids.

Figure 4:
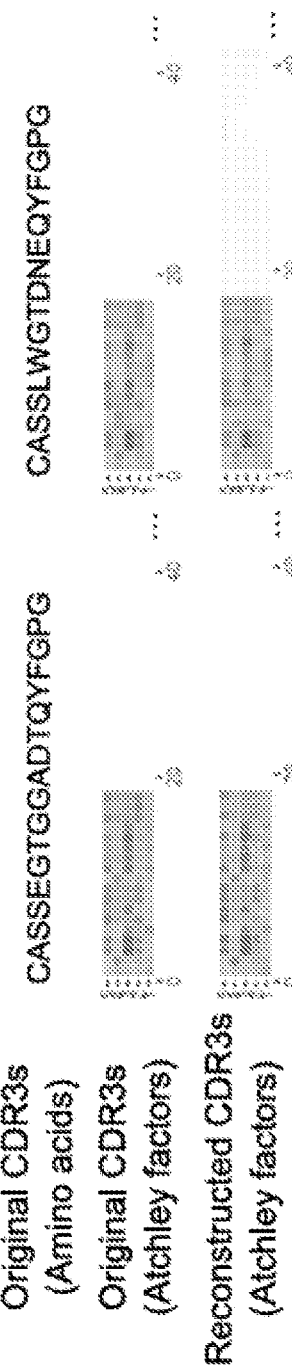
FIG. 4 illustrates exemplary input and reconstructed matrices of the stacked auto-encoder, according to various embodiments of the disclosure.
Figure 5:
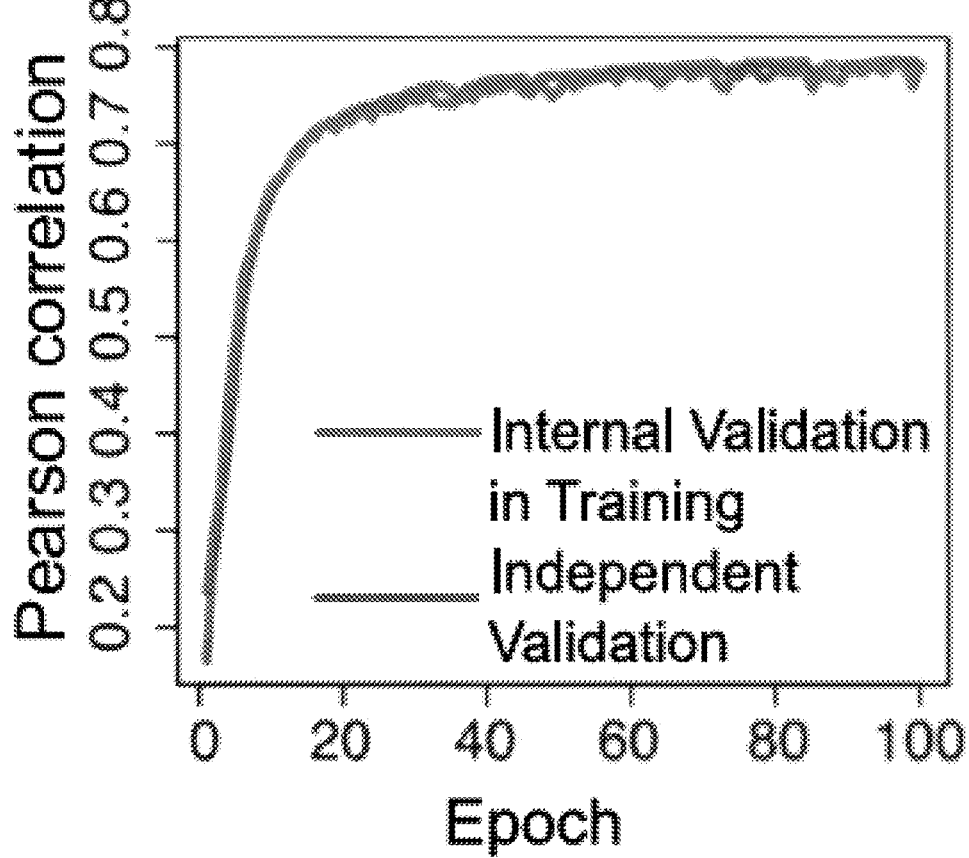
FIG. 5 is a plot showing an exemplary correlation between the input data and the reconstructed data of the stacked auto-encoder, according to various embodiments of the disclosure.

The TCR embeddings may be trained using training data 216 included in database A 212A. The training data 216 for the TCR embeddings may include, for example, 243,747 unique human TCRβ CDR3 sequences. In various embodiments, although only CDR3β sequences are used to train the TCR embeddings, the CDR3s are comprised of V, D and J genes so the information of V and J genes can also be infused into the embeddings. The stacked auto-encoder 224 may be validated by comparing the input Atchley matrices for the TCR sequences received by the encoder layers 302 to the reconstructed Atchley matrices generated by the decoder layers 306. FIG. 4 illustrates the input and reconstructed Atchley matrices for two CDR3s. As shown, the input matrices are very similar to the original input matrices with the Pearson correlations between the original TCR CDR3 Atchley matrices and the reconstructed matrices generally larger than 0.95. FIG. 5 illustrates a plot showing the Pearson correlations between the original TCR CDR3 Atchley matrices and the reconstructed matrices over multiple training epochs. As shown, value of the Pearson correlations increases sharply until around 20 epochs then gradually over additional epochs before plateauing past 80 epochs. The similarity between the input and the reconstructed matrices demonstrates the successful training of the stacked auto-encoder 224.

Figure 6:
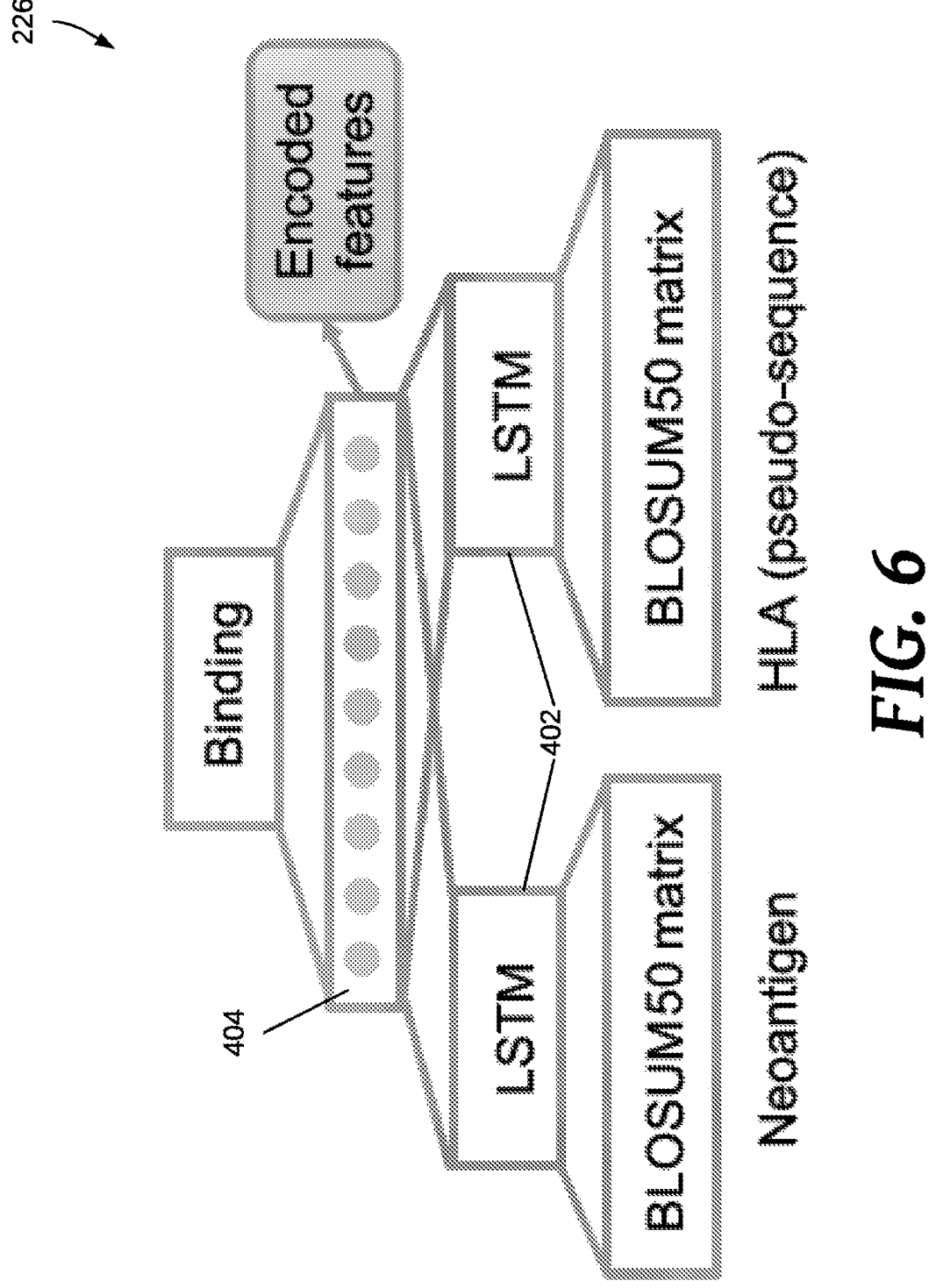
FIG. 6 illustrates an exemplary embedding network included in the machine learning system, according to various embodiments of the present disclosure.

FIG. 6 illustrates more details of the embedding network 226 shown in FIG. 2. The embedding network 226 may train numeric embeddings of pMHCs that represent the protein sequences of neoantigens using a multi-layer neural network. The input of the embedding network 226 may be a group of WIC sequences (e.g., class I MHCs) and a selection of (neo)antigen protein sequences. The output of the embedding network 226 may be a prediction that indicates whether the (neo)antigens bind to the MEW molecule or not. Although the output of the embedding network 226 can be dedicated to predicting antigen and MHC binding, the internal layers of the network may contain important information regarding the overall structure of the pMHC complex. Therefore, features of the pMHC and neoantigens generated by the internal layers of the network may be integrated into the training process used to generate machine learning models for predicting the binding efficiency of pairs of TCRs and pMHCs The embedding network 226 may include one or more deep long short-term memory (LSTM) layers 402 and one or more dense layers 404. To train the pMHCs neoantigen embeddings, a pseudo sequence method may be used to encode the MHC proteins. The pseudo-sequences may consist of the pMHC amino acids in contact with the peptide antigens. Therefore, in various embodiments, a limited number of peptide residues (e.g., 34 polymorphic peptide residues or any other number of residues) may be included in the pseudo-sequences. A Blocks Substitution Matrix (BLOSUM), for example, the BLOSUM50 matrix may be used to encode these 34 residues and the library of neoantigen peptides. The encoding provided by BLOSUM matrices may score alignments between particular protein sequences and encode the input pMHCs and neoantigen peptides with other biological and or chemical information.

The encoded pMHCs and neoantigens may be are input into the LSTM layers 402. To extend, the use of the embedding network to MHC sequence types that are not included in the training data, the MHC sequence instead of the class of MHC (e.g., class I, class II, and the like) may be used as the input into the LSTM layers 402. The LSTM layers 402 may include antigen LSTM layer with an output size of 16 on top of the antigen input, and the MEW LSTM layer may have an output size of 16 on top of the MEW input. The LSTM outputs for antigen and MHC may be concatenated to form a 32-dimensional vector. Including the LSTM layers 402 in the architecture of the embedding network 22 reduces the training time required to generate the learned MEW embeddings by accelerating the timeline for reaching model convergence (i.e., speeding up the convergency process) during training. Including the LSTM layers 402 may also make the features (e.g., the 32 dimensional vector and other features) generated by the internal layers of the embedding network 226 available for integration with the other components of the model architecture used to train the machine learning models. For example, the features (i.e., the WIC and neoantigen embeddings and or features) included in the 32 dimensional vector may be input into a deep neural network that predicts binding efficiency of the MHC with another substance (e.g., TCR sequences)

The LSTM layers 402 may be followed by one or more dense layers 404. For example, a first dense layer (e.g., a dense layer including 60 neurons that is activated by a hyperbolic tangent (tan h) activation function) and second dense layer (e.g., single-neuron dense layer) that follows the first dense layer and serves as the last output layer of the embedding network 226. The output of the second dense layer may be a prediction (e.g., a binding probability) of whether the (neo)antigens bind to the MHC molecule or not.

Figure 7:
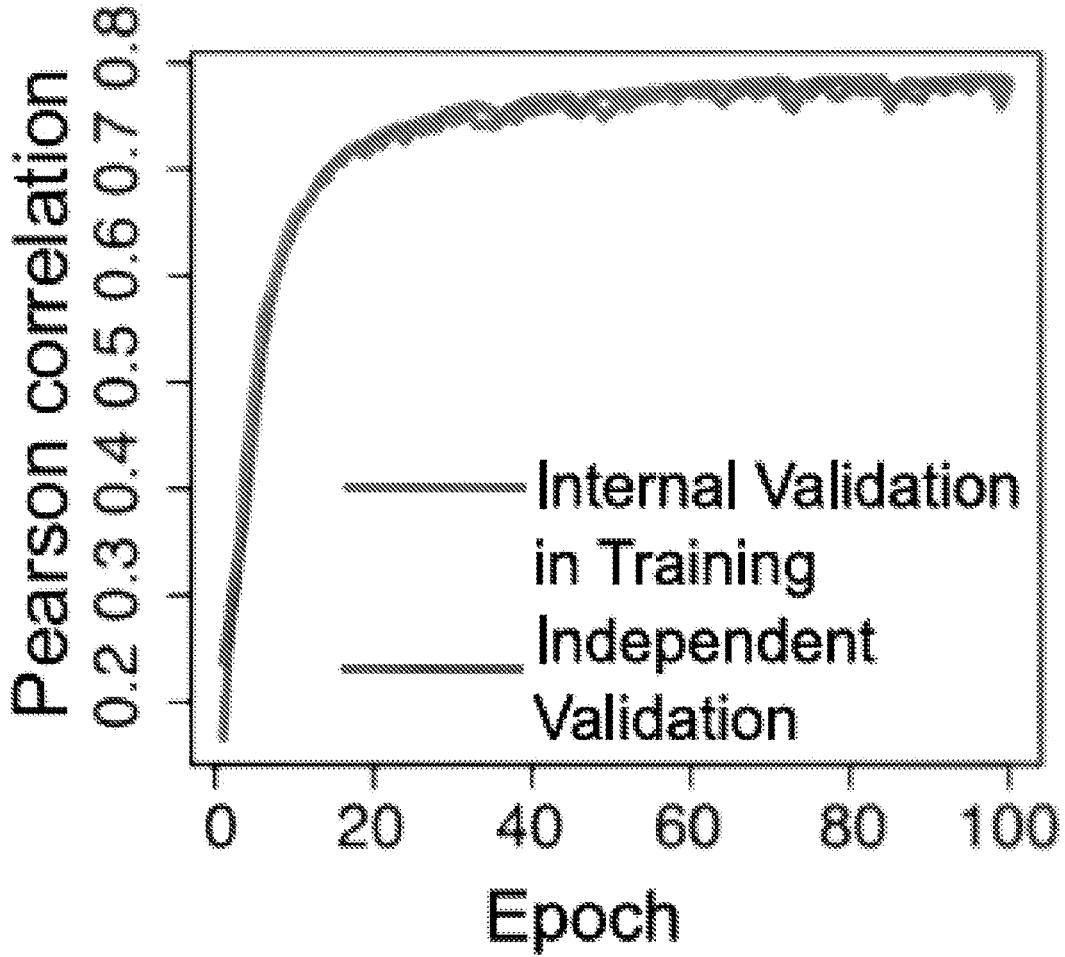
FIG. 7 is a plot showing an exemplary correlation between the predicted bindings generated by the embedding network and known bindings included in a test dataset, according to various embodiments of the present disclosure.

The WIC embeddings may be trained using training data 216 included in database A 212A. The training data 216 for the MHC embeddings may include, for example, 172,422 measurements of peptide-WIC binding affinity covering 130 types of class I MHC from humans. The WIC embeddings generated by the embedding network 226 may be validated by comparing the predicted binding probability generated by the embedding network 226 to a true binding strength for a set of MHCs and neoantigens included in an independent testing dataset. FIG. 7 is a plot of the Pearson Correlation of the predicted binding probability and true binding strength for the independent testing dataset. As shown, value of the Pearson correlation reaches 0.781 after 80 epochs. The value of the Pearson correlation increases sharply until around 20 epochs then gradually over additional epochs before plateauing past 80 epochs. The similarity between the predicted binding probability and true binding strength for the MHC-neoantigen pairs included in the independent testing dataset demonstrates the successful training of the embedding network 226 and the accuracy of the MHC embeddings generated by the intermediate layers of the embedding network 226. After validation, the WIC embeddings may be extracted as a numeric vector from one or more internal layers before the final output layer (e.g., the LSTM layers 402, first dense layer) and may be incorporated to the training process for predicting the binding specificity of TCR and pMHC pairs.

Figure 8:
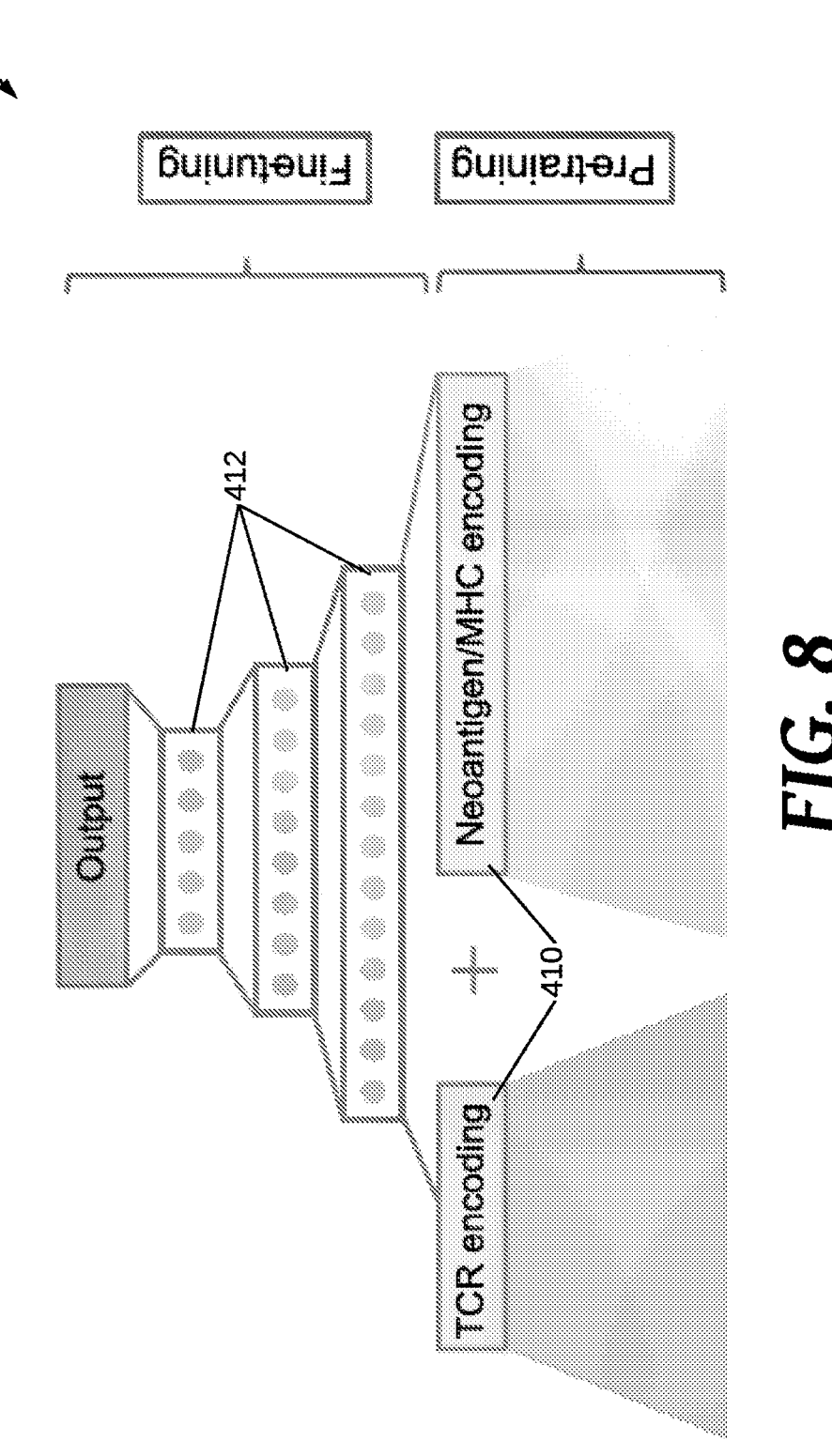
FIG. 8 illustrates an exemplary deep neural network included in the machine learning system, according to various embodiments of the present disclosure.

FIG. 8 illustrates more details of the deep neural network 228 shown in FIG. 2. The deep neural network 228 may include one or more pre-training layers 410 and one or more tuning layers 412. The pre-training layers 410 may generate trained numeric vector encodings of TCRs and pMHCs based on the embedding network and the stacked auto-encoder. The tuning layers 412 may include one or more fully connected layers, pooling layers, dropout layers, and the like that generate a predicted binding specificity for a TCR and pMHC paring.

The pre-training layers 410 may include pre-trained TCR layers that generate TCR encodings and pre-trained MHC layers that generate the neoantigen/MHC encodings. The pre-trained TCR layers may be adapted from the encoder layers of the stacked auto-encoder and the pre-trained MHC layers may be adapted from the LSTM layers of the embedding network. For example, the pre-training layers 410 may be fixed post training of the stacked auto-encoder and the embedding network and may be incorporated into the deep neural network 228 as early layers (e.g., layers positioned before the tuning layers that include saved parameters that are used during training). The TCR and MHC encodings generated by the pre-training layers may be in the form of numeric vectors. The TCR and MHC encodings may then be concatenated into a single layer that feeds into the tuning layers 412.

The tuning layers 412 may include a first dense layer (e.g., a fully connected dense layer with 300 neurons activated by rectified linear unit (RELU) activation layer). The output of the first dense layer may be fed into a dropout layer (e.g., a dropout layer with dropout rate of 0.2) before being fed into two additional dense layers (e.g., a second dense layer with 200 neurons activated by an RELU activation function and a third dense layer with 100 neurons activated by an RELU activation function) The output of the third dense layer may be input into a final output layer (e.g., a dense layer with a single neuron that is activated by an tan h activation function). The final output layer may generate a predicted binding specificity for a TCR-pMHC pair (e.g., for a given pMHC, p*, towards a given TCR, T*) that may be mathematically expressed as f(p*,T*).

In various embodiments, a differential learning schema may be used to train the tuning layers 412 while the pre-training layers 410 may be kept fixed. The differential learning schema may feed a truly binding TCR-pMHC pair and another negative (non-binding) TCR-pMHC pair into the deep neural network 228 during each training cycle. Accordingly, during training, known interactions between binding pMHCs and TCRs may be treated as positive data. The negative pairs may be created by randomly mismatching the known pairs of binding TCRs and pMHCs to create 10 non-interactive pairs for each known interaction (i.e., 10 times more negative data).

The differential learning schema tunes the tuning layers using a differential loss function that trains the deep neural network 228 to differentiate between binding and non-binding TCRs. During each training cycle, a positive and negative TCR-pMHC pair is input into the deep neural network 228. The positive and negative pair may include the same pMHC bound to two different TCRs (e.g., a binding TCR and a non-binding TCR). The composition of the input TCR-pMHC pairs causes the deep neural network 228 to recognize the differences between binding TCRs and non-binding TCRs for specific pMHCs based on a direct comparison between the TCR in the positive (i.e., binding) TCR-pMHC pair and the TCR in the negative (i.e., non-binding) TCR-pMHC pair.

The differential learning schema produces a model that significantly improves the accuracy of binding predictions relative to models trained using other techniques. For example, models developed using learning schemas that group TCRs into clusters that are assumed to be specific to a single epitope are prone to inaccurate binding specificity predictions because these models do not account for the influence pMHCs have on the interactions between epitopes and TCRs. Specifically, pMHCs can restrict the spatial locations and anchor positions of the epitopes thereby impeding binding between a particular epitope and TCR that would otherwise interact in an unrestricted environment. Accordingly, models that do not incorporate pMHCs cannot pinpoint the exact sequence of neoantigens and/or antigens required for a binding interaction. By learning the characteristics of TCRs that bind to specific pMHCs, prediction models trained using the differential learning schema, can predict binding specificity with greater accuracy and precision relative to other models that simply learn the binding labels in the training data and do not learn the characteristics of different TCRs through a direct comparison between a TCR that binds to a particular pMHC and a TCR that does not interact with the same pMHC.

To implement the differential training method, two duplicate deep neural networks 228 may be created with each of the deep neural networks sharing weights throughout the training process. During one example training step, one positive (known interaction) training point (p,T+) is fed into the first network, and a negative training point (p,T−) is fed into the second network. The differential loss function:

$$\text{Loss}=\text{Relu}(f(p,T-)-f(p,T+))+0.03[f2(p,T-)+f2(p,T+)])$$

may then be used to identify TCRs that bind to a particular pMHC. The training process focuses on the same pMHC each time and tries to distinguish between the known interaction TCRs and the negative data points. The second item in the differential loss function may normalize the output of the network to reduce overfitting and push the output of the network to be closer to 0. Normalizing the output ensures the model parameters stay in a dynamic range where gradients are neither too small nor too large.

The output of the deep neural network 228 may be a continuous variable between 0 and 1 that reflects the percentile rank of the predicted binding strength between the TCR and the pMHC, with respect a pool of 10,000 randomly sampled TCRs with the same pMHC. The percentile rank reflects the predicted binding strength of the input TCR and input pMHC relative a background distribution that includes the predicted binding strengths between each TCR in the pool of 10,000 randomly sampled TCRs and the input pMHC. To generate the percentile rank, for each pMHC, p*, evaluated, 10,000 TCR sequences may be randomly selected to form a background distribution, {Tb}. The percentile of f(p*,T*) in the whole distribution of {f(p*,Tb)} may then be calculated, where T* is the TCR of interest. The larger this value, the stronger the predicted binding between p* and T*. The calculated percent of the target TCR within the distribution is then ranked to predict the binding strength between each pMHC and TCR pair with a smaller rank between a pMHC and a TCR corresponding to a stronger binding prediction between them.

To generate the known interaction data and the negative data used to train the deep neural network 228, 32,607 pairs of truly binding TCR-pMHCs may be extracted from one or more publications and or databases. For example, 13,388 known interacting pairs may be extracted from a series of peer-reviewed publications and 19,219 pairs of truly binding TCR-pMHCs may be extracted from four Chromium Single Cell Immune Profiling Solution datasets (N=19,219). Some of the pairs may be associated with one or more quality metrics that describe the interactions between each TCR-pMHC pair. The quality metrics may be used to filter the records. For example, if a database or publication scores the binding interaction between the TCR-pMHC pairs, only the pairs that exceed a particular quality score threshold (e.g., score>0) may be included in the known interaction data. The filtering process may also remove any duplicate records that appear in multiple publications and or databases. To create the negative data each of the 32,607 known interacting pairs may be randomly mismatched.

Figure 9:
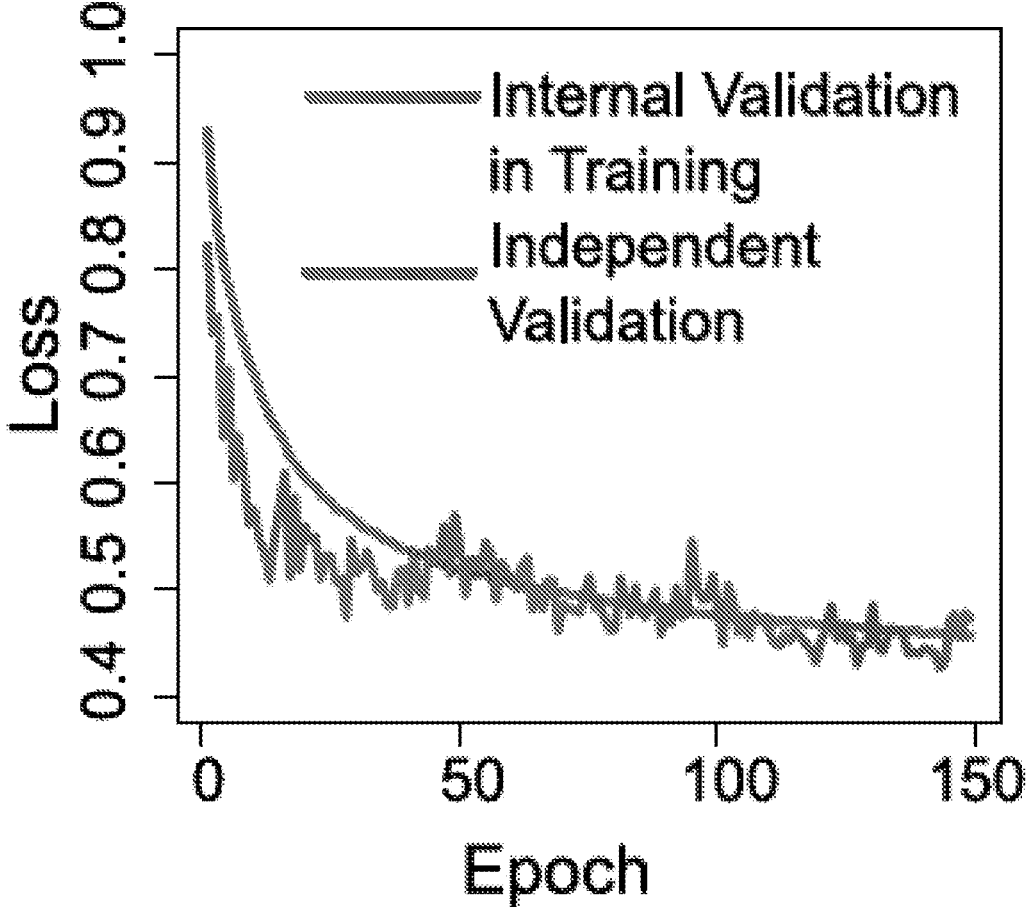
FIG. 9 is a plot illustrating an example loss function over the training period, according to various embodiments of the present disclosure.

The differential training process described above may be performed for 150 epochs. FIG. 9 is a plot illustrating an example loss function over the training period. As shown, the loss function of the training set decreased smoothly, and the loss function of the independent validation set stumbled but closely followed the decreasing trend, demonstrating a good dynamic of the training of model parameters. The antigen and MHC may be bundled together to let the model focus on discerning binding or non-binding TCRs. Accordingly, all the model validations described below may be specific for distinguishing TCR binding specificity, rather than the binding between antigen and MHCs or the overall immunogenicity.

As shown in FIG. 2, the machine learning system 220 may include a training service 230 that assembles training datasets used to fed data to the stacked auto-encoder 224, the embedding network 226, and the deep neural network 228 during training. To assemble the training datasets, the training service 230 may retrieve TCR sequences, pMHC-TCR pair data, and other training data 216 from one or more databases included in the data storage system 210. For example, the training service 230 may submit a query to a training data API 214 that requests particular pieces of training data 216 from one or more of the databases 212A, . . . , 212C (e.g., database A 212A). The training service 230 may train the machine learning models 229 by providing the training data 216 to the stacked auto-encoder 224, embedding network 226, deep neural network 228, or other components of the model architecture 222 and executing one or more of the training processes described above.

Learned features 218 generated during model training may be collected by the training service 230 and stored in one or more of the databases 212A, . . . , 212C of the data storage system 210. For example, TCR encodings generated by the stacked auto-encoder 224, neoantigen/MHC encodings generated by the embedding network 226, and other feature vectors generated during training of the machine learning models 229 may be stored as learning features 218 in database C 212C. The learning features 218 may be used as inputs in one or more training process to transfer knowledge from the learned features into the trained models. The data stored in the data storage system may be continuously updated to ensure the most recent experimental and or clinical data is used to train the machine learning models. To improve the accuracy of the machine learning models 229, the training service 230 may re-train the stacked auto-encoder 224, embedding network 226, deep neural network 228, and or other components of the model architecture 222 using new experimental and or clinical data that is added to the data storage system. For example, the training service 230 may assemble training datasets that include TCR sequences and pMHC-TCR pair data included in new clinical data that confirms the binding of certain TCRs to tumor neoantigens. The training service 230 may expand the training dataset for the stacked auto-encoder 224 by adding the TCR sequences included in the new clinical the existing training data for the TCR encodings. The training service 230 may then re-train the stacked auto-encoder 224 using the expanded training dataset to generated updated TCR encodings that include insights derived from the additional TCR sequence data. The training service 230 may the re-train the deep neural network using the updated TCR encodings to improve the accuracy of predicted binding specifies for input pMHC-TCR pairs that are similar to the TCRs and or tumor neoantigen included in the new clinical data. Re-training one or more components of the model architecture 222 may generate new machine learning models 229 that are more accurate and/or perform better than the previous iteration of the machine learning models 229.

To generate the binding specificity predictions 234, the machine learning system 220 may include a prediction engine 232 that inferences the machine learning models 229. For example, the prediction engine 232 may receive a prediction request from an API or other endpoint and or a remote device that includes one or more pMHC-TCR pairs having an unknown binding specificity. The prediction engine 232 may run inference on the machine learning models 229 for the one or more pMHC-TCR pairs included in the prediction request to generate a binding specificity prediction 234 for each of the pMHC-TCR pairs.

To determine the accuracy of the binding specificity predictions 234 generated by the machine learning models 229, the binding specificity predictions 234 may be validated experimentally using the validation engine 236. For example, the validation engine 236 may assemble validation data 217 including one or more pMHC-TCR pairs that are not included in the training data 216. The validation engine 236 may then run inference on the validation data 217 using the machine learning models 229 to generate binding specificity predictions 234 for the pMHC-TCR pairs included in the validation data 217. The binding specificity predictions 234 for the MHC-TCR pairs included in the validation data 217 may be compared to known binding interactions for the pMHC-TCR pairs to determine accurate predictions (i.e., binding specificity predictions that match the known binding interactions) and inaccurate predictions (i.e., binding specificity predictions that do not match the known binding interactions). The accurate predictions and inaccurate predications generated during model validation may be stored as learning features 218 that may be used to improve the accuracy of the machine learning models 229. For example, one or more parameters (e.g., learning rate, learning algorithm, training hyperparameter, and the like) and or learned features of the stacked auto-encoder 224, embedding network 226, and or deep neural network 228 may be modified based on the previously generated predictions. The training service 230 may then re-train the modified components of the model architecture 222 to generate a new iteration of machine learning models 229. The validation engine 236 may then repeat the validation process on the new machine learning models 229 to determine if the modifications reduced the number of inaccurate predictions. The cycle of modifying the components of the model architecture 222, re-training the components of the model architecture 222 to generate a new iteration of machine learning models 229, and validating the new iteration of machine learning models 229 may be repeated until the accuracy of the machine learning models 229 meets or exceeds a pre-determined accuracy threshold.

Model Validation Examples

Example 1—Predicting TCR-pMHC Pairings in Experimental Data

To validate the prediction accuracy of the machine learning models a series of validation assays may be performed. To validate the machine learning models experimentally a validation dataset of 619 experimentally validated TCR-pMHC binding pairs were compared. Each of the TCR-pMHC binding pairs included in the validation dataset may be subjected to stringent interrogation by independent researchers and may be manually curated. The TCR-pMHC pairs included in the validation dataset were filtered against the training dataset to remove any pairs that appeared in the training dataset so that the validation datasets are completely independent of the training data. 10 times negative pairs were generated by random mismatching.

Figure 10:
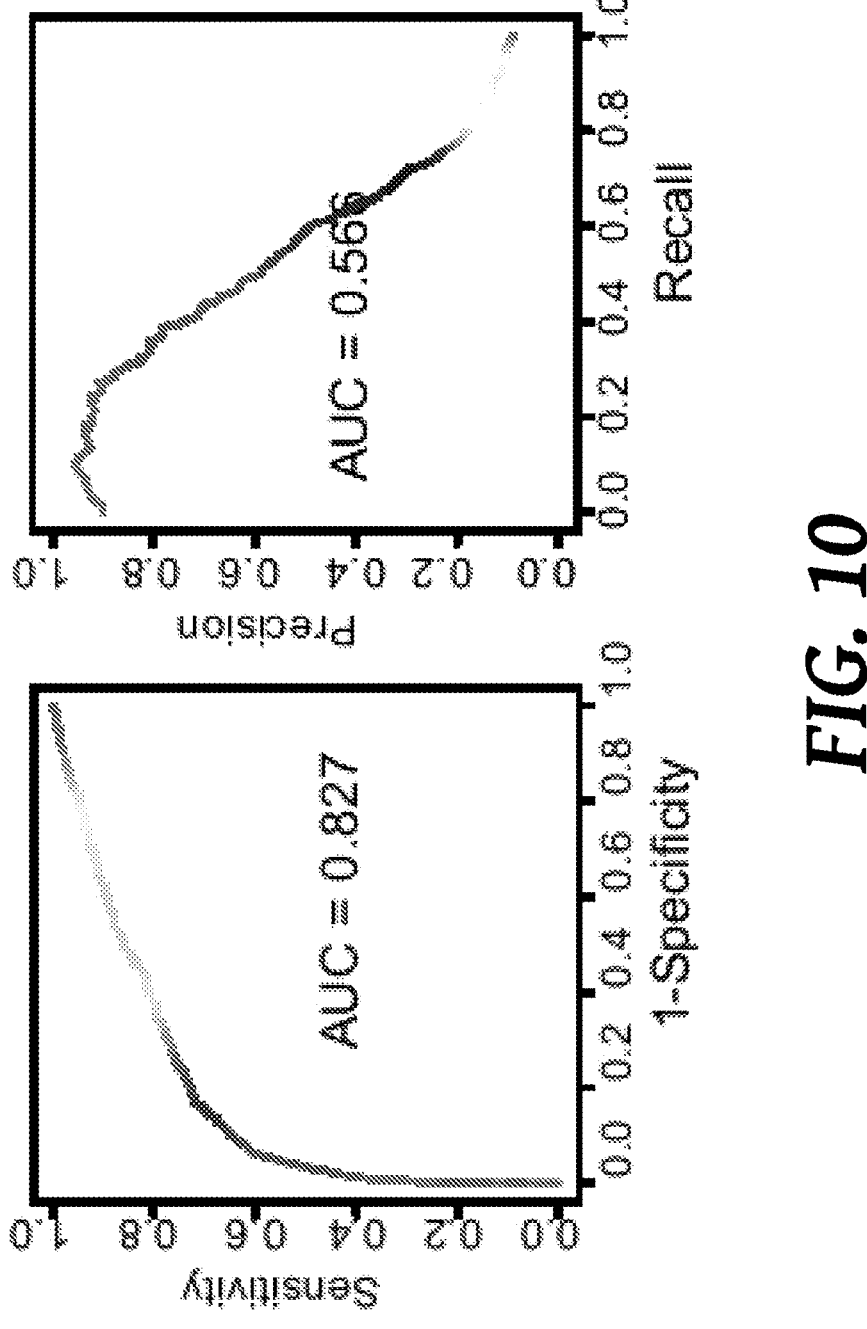
FIG. 10 is a pair of plots illustrating the performance of the machine learning models during a binding specificity prediction task, according to various embodiments of the present disclosure.

To determine the sensitivity and recall of the machine learning models, a binding specificity prediction for each TCR-pMHC pair included in the validation dataset was generated by the machine learning model. The predicted specificity predictions for validation TCR-pMHC pairs were then compared to known binding interactions. The results of the comparison are shown in FIG. 10 with the left plot including a receiver operating characteristic (ROC) and the right plot indicating precision-recall. The ROC plots the model's true positive rate (sensitivity) against the false positive rate (1−specificity) for the predictions on the validation dataset. As shown, the area under the curve (AUC) for the ROC is 0.827 indicating the model successfully distinguishes between positive (binding) and negative (non-binding) predictions 83% of the time. The right plot includes a Precision-Recall (PR) curve that plots the precision of the model (i.e., the number of correct positive predictions (binding predictions) made) against the recall of the model (i.e., the number of correct positive predictions made out of all positive predictions that could have been made. As shown, the AUC for the PR curve is 0.565

Figure 11:
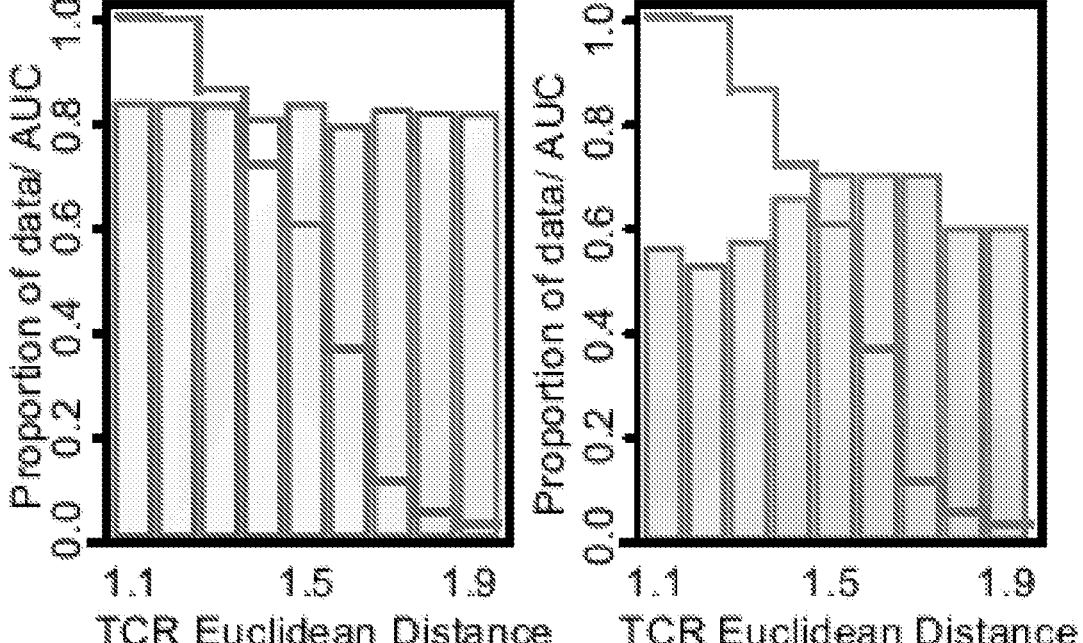
FIG. 11-12 are plots illustrating the performance of the machine learning models when predicting the binding specificities of increasingly dissimilar TCRs, according to various embodiments of the present disclosure.
Figure 12:
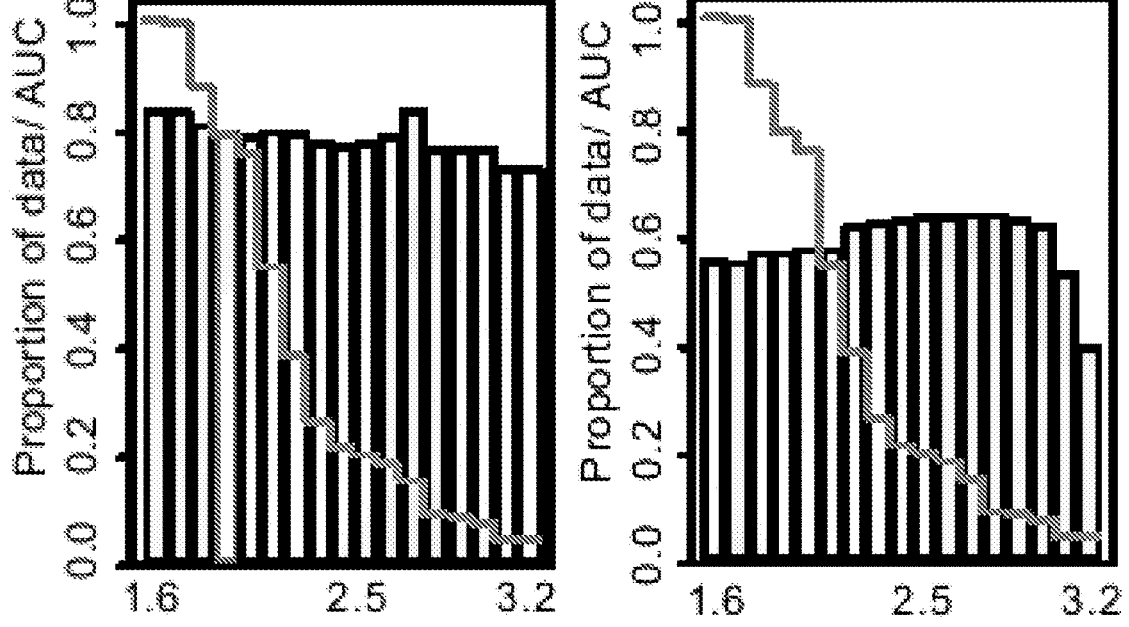

To test whether the machine learning model truly "learned" the features that determine binding, or is simply "remembering" pairing cases, we looked at the prediction performance for TCRs with different degrees of similarity to the TCR sequences included in the training dataset. To calculate "similarity" of the TCR sequences, the minimum Euclidean Distance for each TCR included the validation dataset relative to all the TCR sequences included in the training dataset were calculated based on the TCR embeddings. FIGS. 11-12 each include a pair of plots that illustrate the AUCs of ROC (left plot) and PR (right plot) for the subset of the validation TCRs with minimum distances over each cutoff (e.g., a Euclidean Distance of 1.0). FIG. 11 includes two plots that illustrate the AUCs of ROC (left plot) and PR (right plot) for the subset of the validation pMHCs with minimum distances over each cutoff (e.g., a Euclidean Distance of 1.5) between a Euclidian Distance of 1.1 and 1.9. FIG. 12 illustrates two plots that illustrate the AUCs of ROC (left plot) and PR (right plot) for the subset of the validation TCRs separated by a greater minimum distances (e.g., a range of cutoffs between an Euclidian Distance 1.6 and 3.2. As shown in the plots of FIGS. 11 and 12, the performance of the machine learning models is robust with respect to increasing levels of TCR dissimilarities. The same analysis may be performed for the pMHCs included in the validation dataset.

Relative to other software that can predict TCR/epitope pairing, the machine learning models disclosed herein are not limited by the types of epitopes/MHCs/TCRs (e.g., HLA-A:0201 allele, epitopes shorter than 10 amino acids, and CDR3 shorter than 10 amino acids) that can be used for prediction. Accordingly, the validation dataset used for experimental validation may include a diverse set of different epitopes/MHCs/TCRs that violate one or more of the conditions of other pairing prediction software. The ability of the machine learning models described herein to maintain performance across the entire validation dataset demonstrates the flexibility of the machine learning models generated by the disclosure and is a significant advance over the more limited other prediction software.

Example 2—Evaluating the Expected Impact of the Predicted Binding on T Cells The predicted binding between TCRs and pMHCs was also validated based on the expected impact of the binding on the T cells. In particular, the clonal expansion of T cells was evaluated to determine if the T cells with higher predicted pMHC affinity were more clonally expanded. To generate the clones, the 10× Genomics Chromium Single Cell Immune Profiling platform was used to generate single cell 5' libraries and V(D)J enriched libraries in combination with highly multiplexed pMHC multimer reagents. The antigen specificity between the TCR of one T cell and each tested pMHC was then profiled by counting the number of barcodes sequenced for that particular pMHC in this cell. The predicted binding was evaluated based on four single-cell datasets, which profiled the antigen specificities of 44 pMHCs for CD8+ T cells from four healthy donors. Across all four donors, a total of 189,512 T cells corresponding to 68,171 unique TCR clones were obtained. For each of these TCR clones, the pMHC with the strongest predicted binding strength among all 44 pMHCs was recorded.

Figure 13:
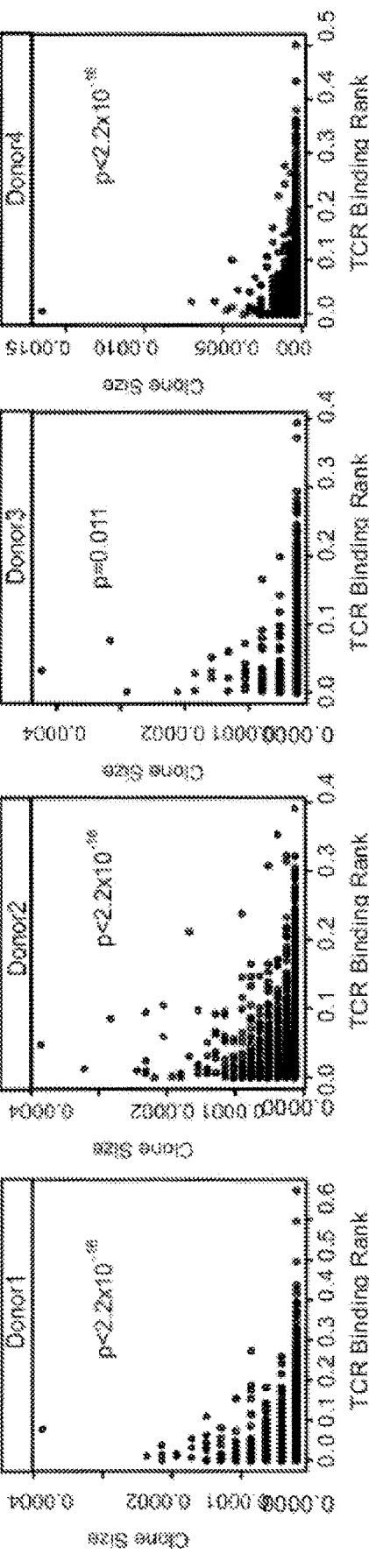
FIG. 13 includes a set of plots illustrating the clonal expansion the pMHC with the strongest predicted binding strength for different donors, according to various embodiments of the present disclosure.

FIG. 13 illustrates the clonal expansion size of the TCRs and their relative pMHC binding rank for each of the 4 donors. As shown, the clone sizes and predicted ranks for the T cell clonotypes were negatively correlated. In particular, the Spearman correlation between the clone sizes and predicted TCR binding ranks was −0.202, −0.334, −0.178, and −0.214, respectively with statistical significance achieved for each of the 4 donors. Therefore, T cells with TCRs having predicted pMHC binding strengths that are stronger have smaller clone sizes than the other T cells without a strong binding partner. Additionally, some TCRs with small clone sizes having small predicted binding ranks with a pMHC were also observed. The corresponding relationship between close sizes and predicted binding ranks to pMHCs in some cases is likely caused by the stochastic nature of the binding between TCRs and pMHCs, and possibly the constantly incoming new clones whose expansion has not happened yet.

Figure 14:
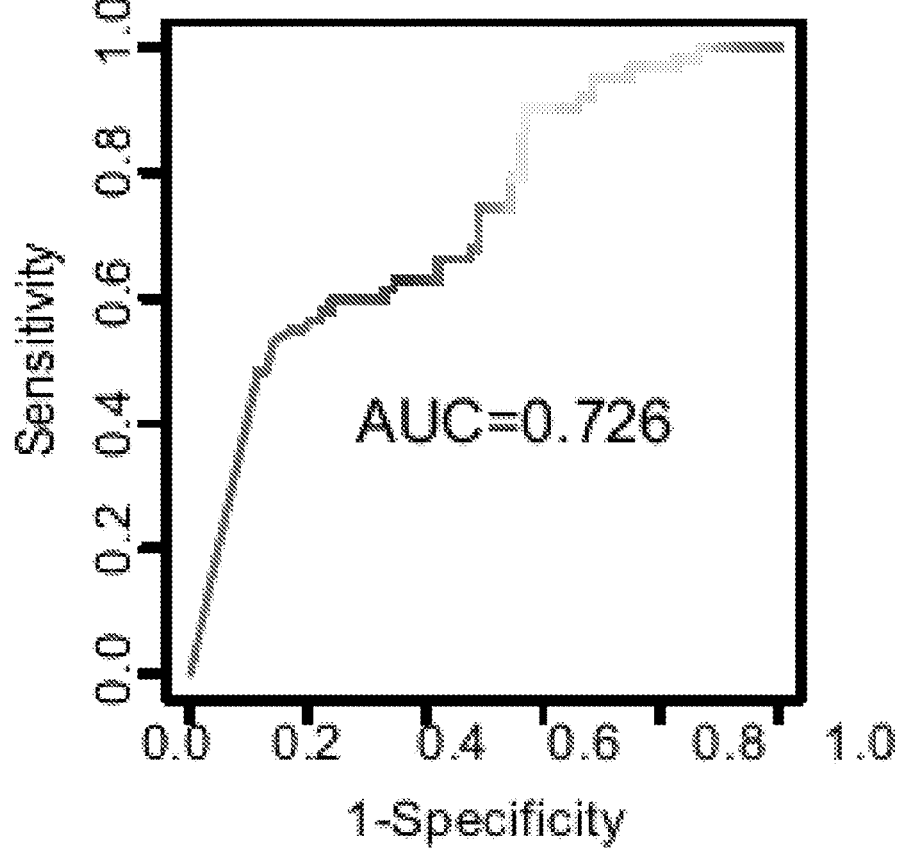
FIG. 14 is a plot illustrating the performance of the machine learning models when predicting the binding specificity between a set of peptide analogs and three distinct TCRs, according to various embodiments of the present disclosure.

The ability of the machine learning model to distinguish the impact of the fine details of the peptide sequences on their TCR binding specificity was also investigated. To validate the model's ability to predict binding specificity based on the fine details of peptide sequences, 94 pMHC-TCR pairs were acquired from a previous study conducted by Liu et all. In this study, LPEP peptide analogs with single amino acid substitutions were tested for specificity towards three distinct TCRs with different CDR3β and binding mechanisms with pMHC. Out of all 94 analogs, 36 were determined as stronger binders (<100 pM of peptide needed to induce cytotoxic lysis by T cell) and the others as weaker binders. The machine learning model generated a prediction for each of the 94 peptide analogs (in complex with MHC) and the 36 strong binding analogs were predicted to have stronger binding strength than the rest analogs. FIG. 14 illustrates the AUC for the ROC of the predictions generated for the peptide analog validation dataset is 0.726 indicating the model successfully distinguishes between positive (binding) and negative (non-binding) predictions 73% of the time. The same analysis was also performed on another set of pMHC analogs from Cole et ah. In this cohort, the stronger binding pMHCs were also predicted to have stronger binding strength than the other analogs with the AUC of the ROC for this validation dataset being 0.682.

Example 3—Predicted Binding on Prospective Experimental Data

Figure 15:
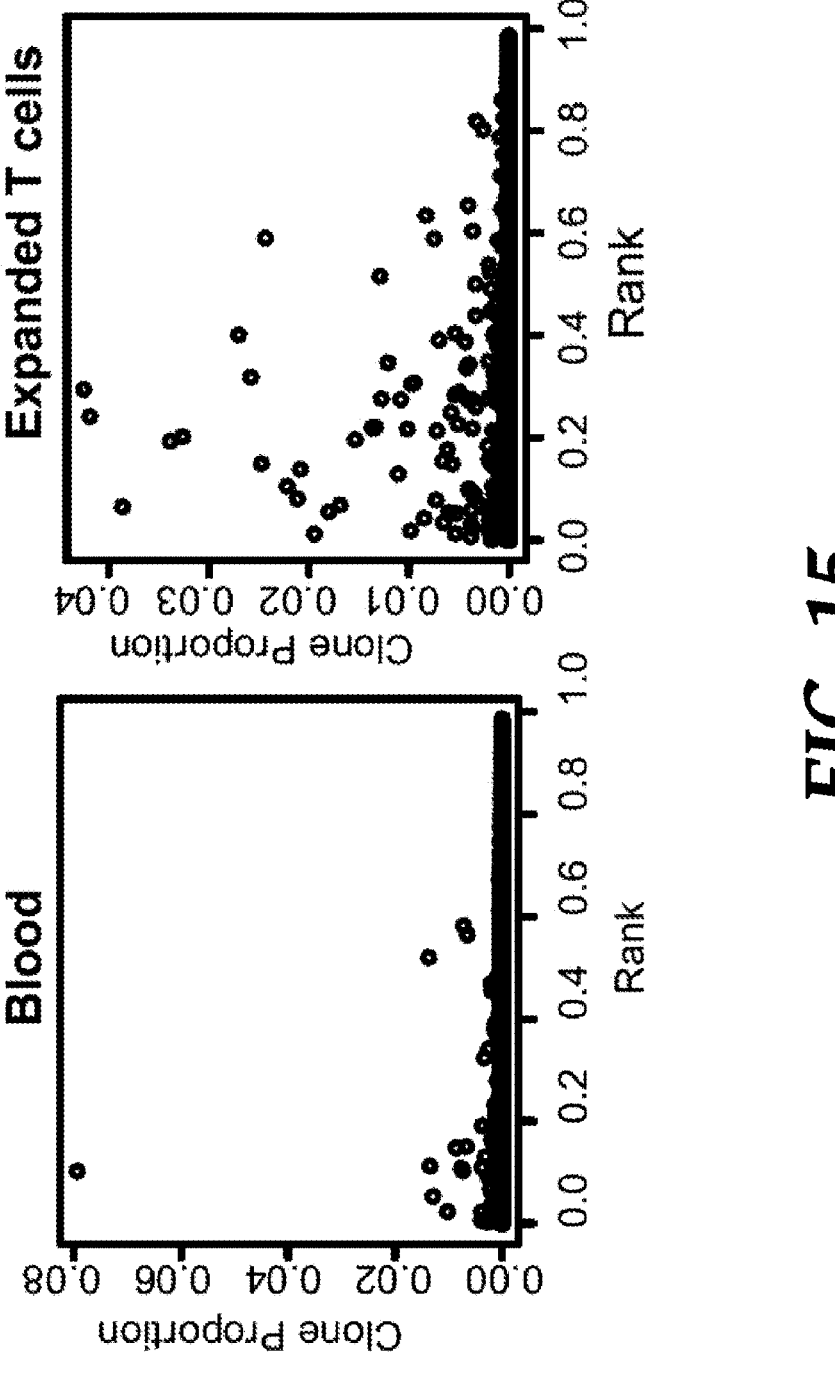
FIG. 15 is a plot illustrating a ranking of the binding predictions between four viral pMHCs and TCR sequences isolated from the blood and T cell samples of a patient, according to various embodiments of the present disclosure.

The machine learning model was also validated using a prospective experimental dataset. To obtain the prospective experimental dataset bulk TCR-sequencing and HLA allele typing was performed for one donor seropositive for prior Influenza, EBV and HCMV infections. The experiments were performed in the blood and the in vitro expanded T cells from the donor's lung tumor. The bulk TCR-sequencing data was analyzed and the binding between the sequenced TCRs and four viral pMHCs, (e.g., Influenza M (GILGFVFTL), Influenza A (FMYSDFHFI), EBV BMLF1 (GLCTLVAML), and HCMV pp65 (NLVPMVATV)) was predicted using the machine learning model. FIG. 15 is a plot illustrating a ranking of the binding predictions for TCR sequences obtained from the blood (left plot) and T cell (right plot) samples. As shown, TCRs predicted to have stronger binding (i.e., smaller ranks) to any of the 4 viral peptides exhibited higher clonal proportions than the other TCRs, in both the blood and in vitro expanded T cells.

Figure 16:
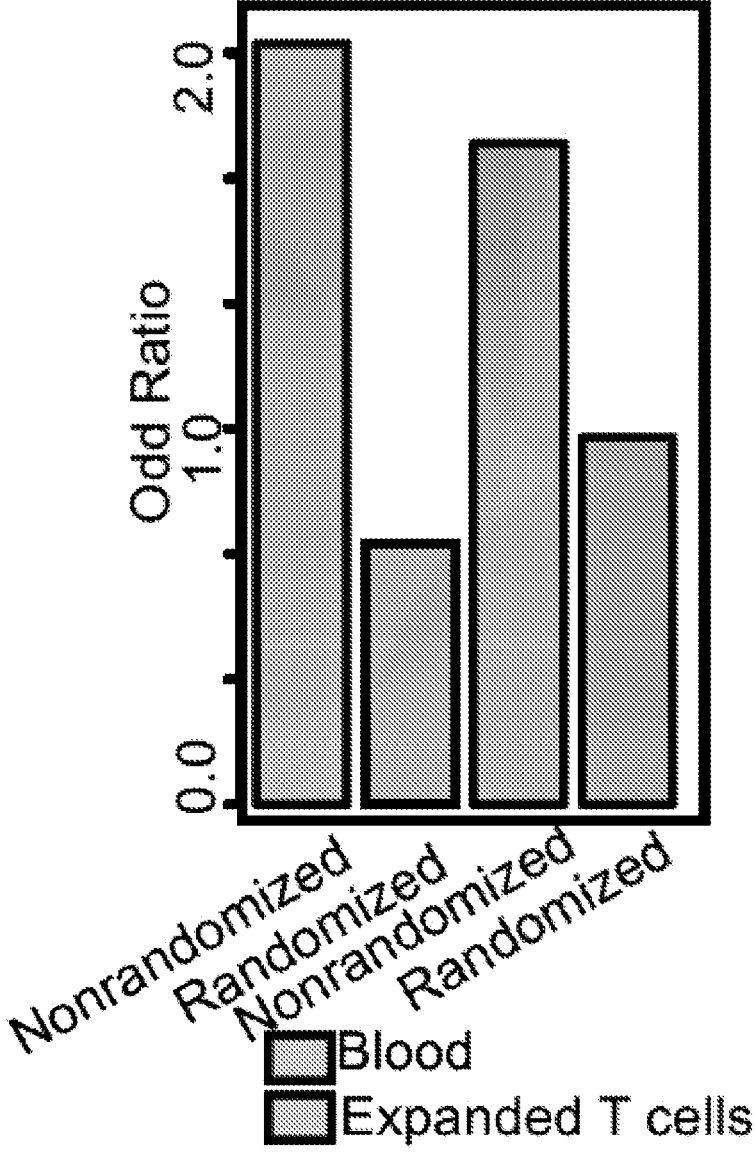
FIG. 16 is a graph illustrating the odds ratios calculated for the enrichment of highly expanded TCRs, according to various embodiments of the present disclosure.

To further evaluate the TCRs with stronger predicted binding, the odds ratios for the enrichment of highly expanded TCRs with stronger predicted binding were calculated. In this analysis, a higher odds ratio refers to a higher positive enrichment and a lower odds ratio corresponds to a lower positive enrichment. FIG. 16 is a graph illustrating the odds ratios calculated for the enrichment of highly expanded TCRs with the left two columns corresponding to the TCRs isolated from blood and the right two columns corresponding to TCRs isolated from the T cells. As shown, a stronger enrichment in both the nonrandomized TCRs in the blood and expanded T cells. Conversely, random permutations of the predicted binding ranks produced much smaller odds ratios.

Figure 17:
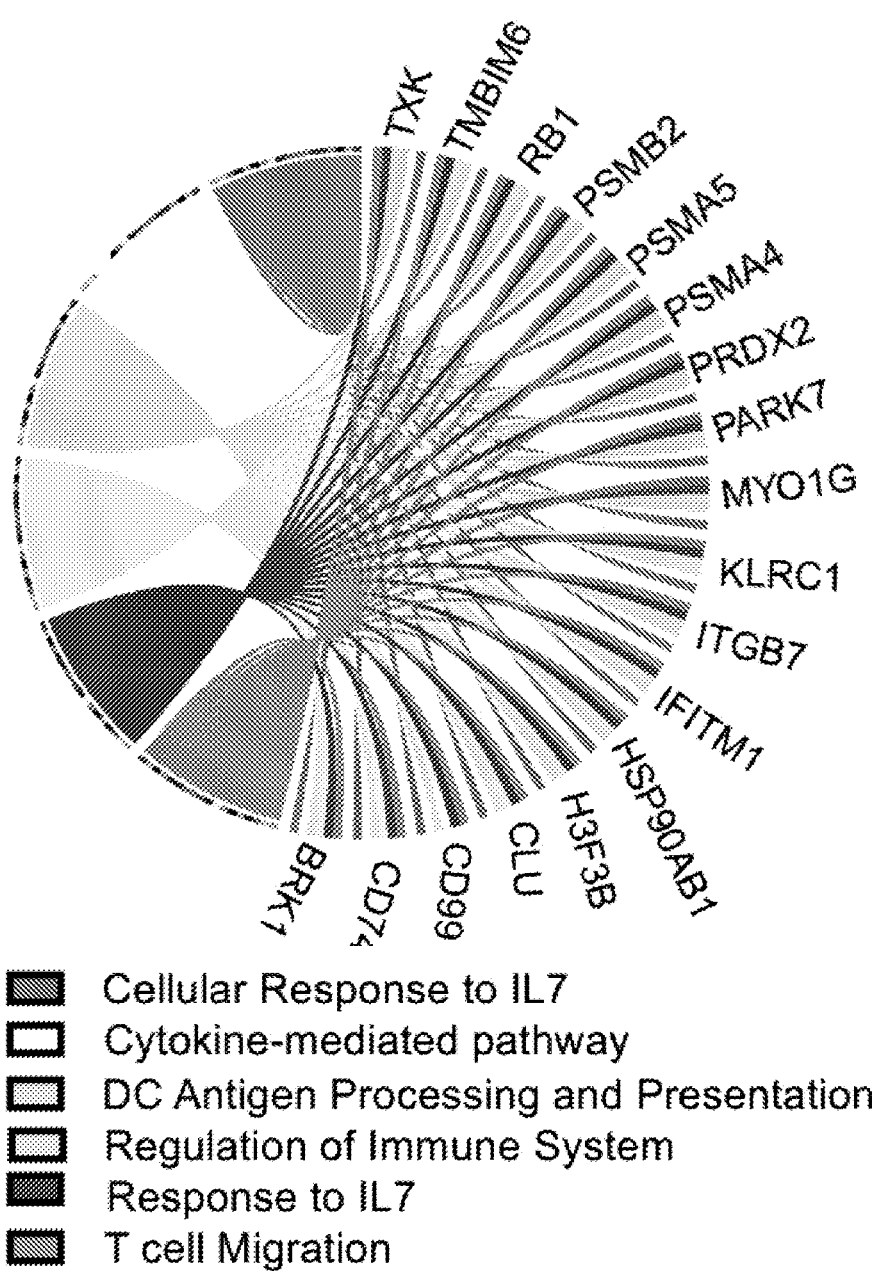
FIG. 17 is a chart illustrating the results for the top ranked TCRs bindings with a particular viral pMHC, according to various embodiments of the present disclosure.
Figure 18:
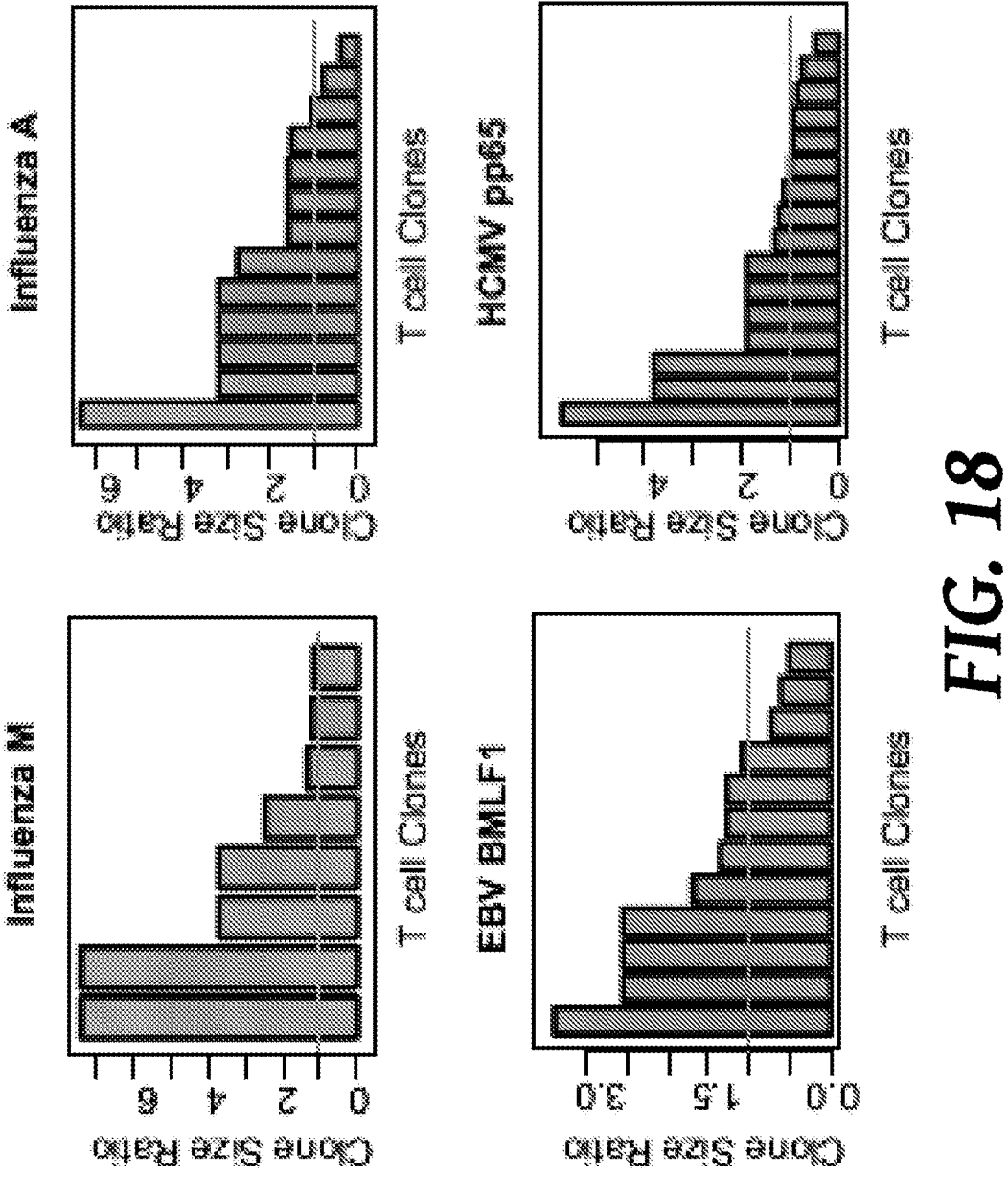
FIG. 18 is a set of graphs illustrating the clonal sizes of the top TCR clonotypes for each of the viral peptides, according to various embodiments of the present disclosure.

The expanded T cells were then treated with each of the viral peptides. To document the binding specificity of the expanded T cells scRNA-seq with paired TCR-seq and vehicle treatment were performed. TCRs captured in each of the treatment groups and the vehicle treatment group were then identified and input into the machine learning model to obtain a predicted binding of the identified TCRs to each peptide. The top TCRs (predicted rank<2% by the machine learning model) were selected from each experiment. To evaluate the highest ranked TCRs, the gene expression of the T cells of these top binding TCR clonotypes for each of the viral pMHCs was examined by comparing T cells with predicted top binding TCRs and the other T cells isolated from the sample. The comparison revealed differentially expressed genes enriched in pathways essential for T cell proliferation, migration, survival, and cytotoxicity. FIG. 17 is a chart illustrating the results for the top ranked TCRs bindings with GLCTLVAML The clonal sizes of these top TCR clonotypes were also calculated. FIG. 18 is a graph illustrating the clonal sizes of the top TCR clonotypes for each of the viral peptides. As shown, the majority of the top TCR clonotypes exhibited larger clonal fractions in the treatment group than the vehicle group.

Example 4—Structural Analyses of the Predicted TCR-pMHC Interactions

Figure 19:
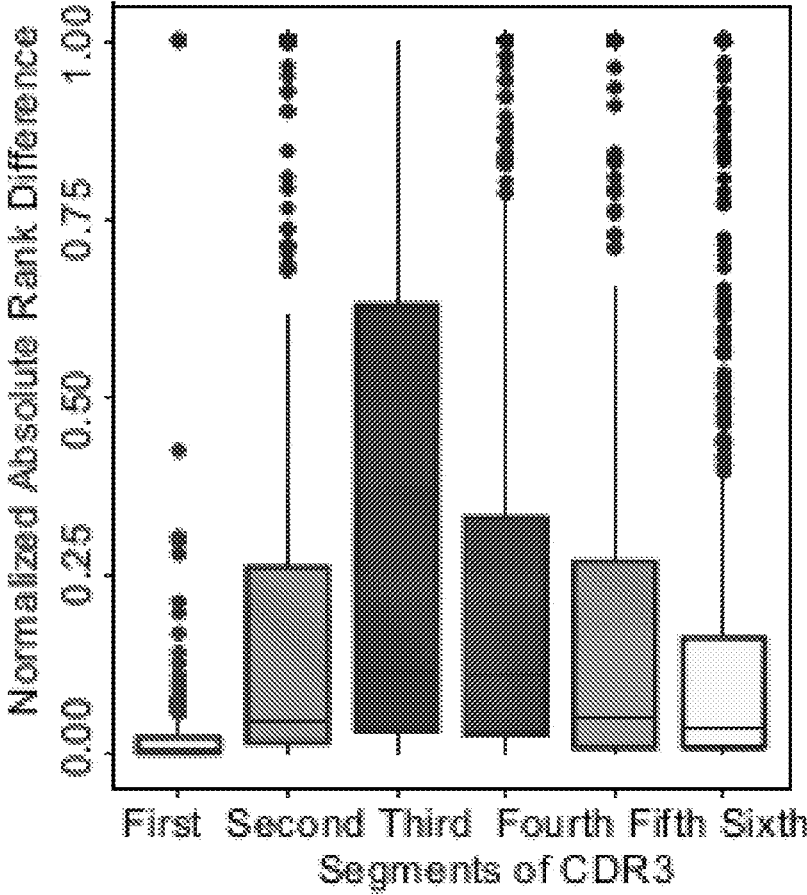
FIG. 19 is a graph illustrating the rank differences for different segments of TCR sequences, according to various embodiments of the present disclosure.

Mutational analyses were also performed to identify structural characteristics of CDR3 residues whose mutations led to dramatic changes in the predicted binding between TCR and pMHCs. To identify structural characteristics of CDR3 residues that influence predicted binding specificity, the numeric embedding of each CDR3 residue was mutated to a vector of all 0s ("0-setting"). The residue mutations were performed for all the 619 TCRs included in the testing cohort of the validation data. The differences in the predicted binding ranks (rank difference) between the wild type TCRs and the mutated TCRs were then recorded. FIG. 19 is a graph illustrating the rank differences for different segments of the TCR CDR3. As shown, each TCR CDR3 was divided into six segments of equal lengths and residues in the middle segments of CDR3 s, which bulge out and are in closer contact with pMHCs, are more likely to induce larger changes in predicted binding affinity, when compared with the outer segments (i.e., contribute more to the measured rank difference). T test P value between the third or fourth segment and any other segment is <0.00001).

Figure 20:
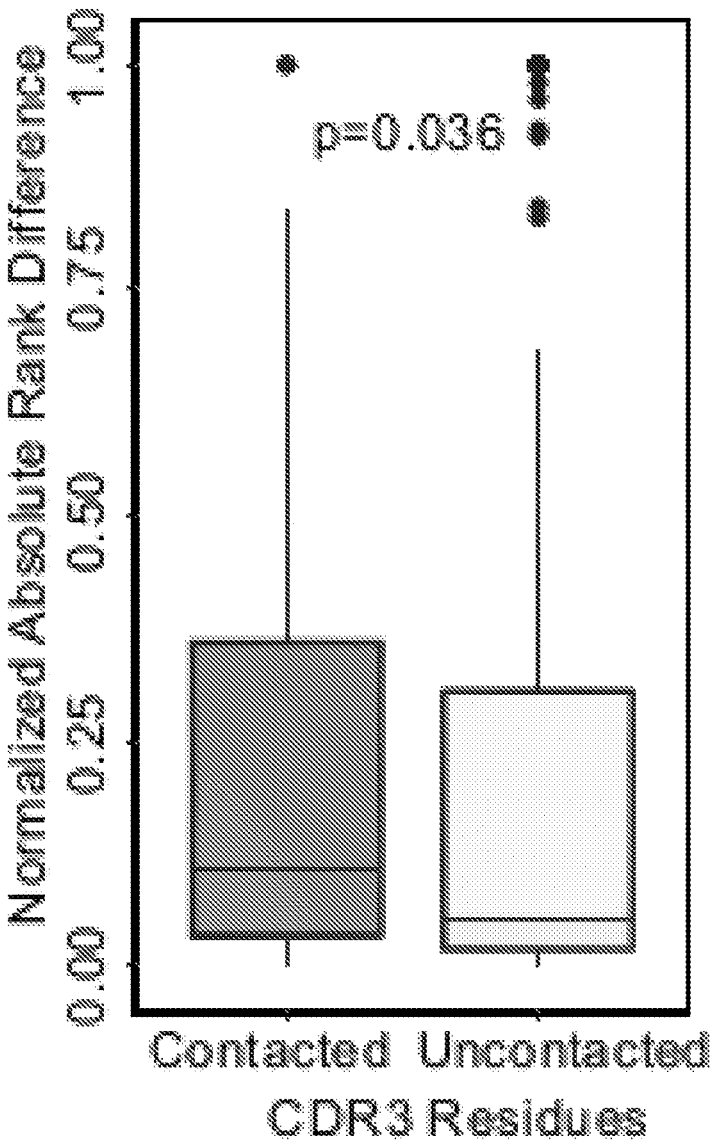
FIG. 20 illustrates the contribution to rank difference of the TCR residues in contact with pMHC residences and the TCR residues that are not in contact with pMHC residues, according to various embodiments of the present disclosure.

Additional mutational analysis were performed on 13 TCR-pMHC pairs extracted from the IEDB cohort. The extracted TCR-pMHC pairs all had a predicted binding affinity less than 2%. The 3D crystal structures were then analyzed from each of the 13 pairs. Based on the structures, the CDR3 residues were group by whether or not they formed any direct contacts with any residues of pMHCs within 4 Å. FIG. 20 illustrates the contribution to rank difference of the contacted residues and the uncontacted residues. As show, the contacted residues are more likely to induce larger changes in the predicted pMHC binding strength than non-contacted residues (P value=0.036). In silico alanine scanning was also performed and revealed a similar trend. The P value for alanine scan is not as significant as for the "0-setting" scan, which could be partially attributed to the fact that, in alanine scan, all alanines will be judged to have no effect after mutation (alanine→alanine). However, replacing one alanine with other residues with large side chains could affect the overall structural integrity of the protein complex, which may actually lead to a loss of binding affinity.

Figure 21:
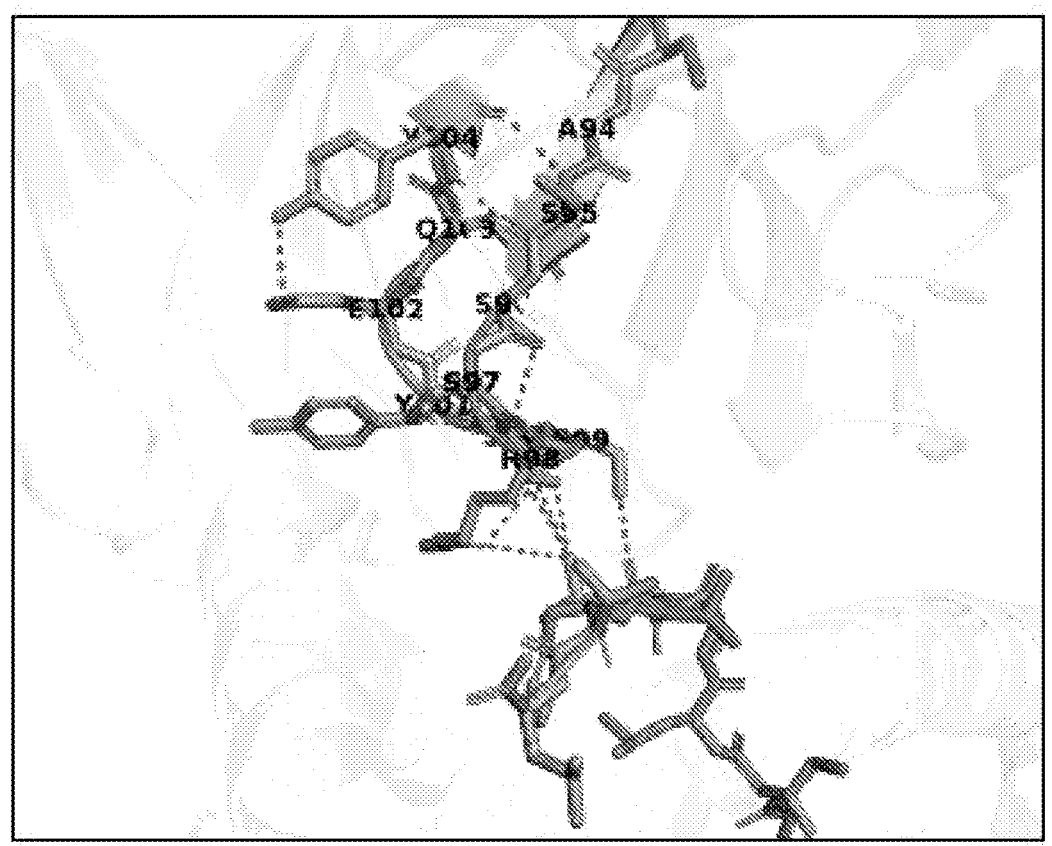
FIG. 21 illustrates an example TCR-pMHC structure, according to various embodiments of the present disclosure.
Figure 22:
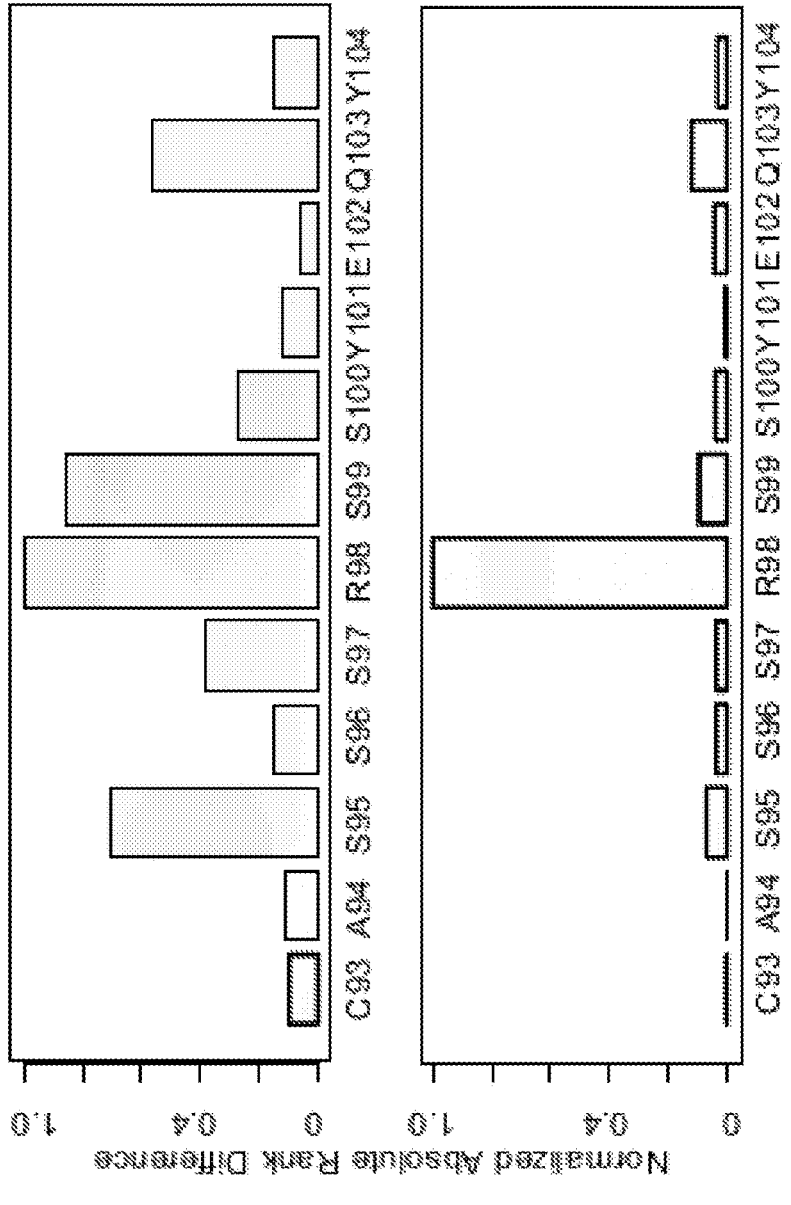
FIG. 22 is a graph summarizing the contribution of each portion of the TCR-pMHC structure to the predicted binding rank, according to various embodiments of the present disclosure.

FIG. 21 illustrates an example TCR-pMHC structure with the PDB (Protein Data Bank) id of 5 hhm, generated by Valkenburg et al[3]. FIG. 22 is a graph summarizing the contribution of each portion of the TCR-pMHC structure to the predicted binding rank. As shown in the upper graph, R98 and S99 had the biggest differences in predicted ranks after the "0-setting" scan. As shown in the lower graph, R98 and S99 also had the biggest differences in predicted ranks after the alanine scan. As shown in the structure of FIGS. 21, R98 and S99 are the residues located in the middle of the CDR3 and therefore had the most contacts with pMHC. The other two amino acids with relatively high rank changes could be explained by their crucial role in formation and stabilization of the CDR3 loop. For example, S95 is known to form intra-chain contacts with the small loop formed by Q103 and the side chains of E102 and Y104. These results indicate that the composition of the portions of the TCR that interact with the pMHC the most during binding have the greatest impact on the predicted binding generated by the model. Accordingly, it appears the machine learning model is able to accurately distinguish the portions of the TCR that have the most contact with the pMHC and generate binding predictions primarily based on the composition of these portions.

Example 5—Characterizing the TCR-pMHC Interactions in Human Tumors Based on Predicted Bindings To validate the machine learning model as a knowledge discovery tool, the TCR and pMHC interactions were characterized in several of the immunogenic tumor types, where the T cell-tumor antigen machinery is more likely to be active. To characterize the TCR and pMHC interactions in the different tumor types, the genomics data of The Cancer Genome Atlas (TCGA) and UTSW Kidney Cancer Program (KCP) patients with Renal Cell Carcinoma (RCC) was analyzed. The patients included in the TCGA dataset included lung adenocarcinoma patients (LUAD), lung squamous cell carcinoma patients (LUSC), clear cell renal cell carcinoma patients (KIRC), and melanoma patients (SKCM).

Multiple factors can induce T cell infiltration in the tumor microenvironment. For example, one portion of the T cell infiltration may be accounted for by tumor neoantigens. T cell infiltration may also be induced by tumor self-antigens, such as CAIX. In kidney cancer, in particular, Cherkasova et al[4] discovered the re-activation of a HERV-E retrovirus, which encodes several immunogenic peptides that have been experimentally validated[39]. T cell infiltration may also be influenced by prior virus infection, or the infiltrating T cells may simply be bystanders. Which of these factors is most potent in inducing T cell infiltration is an open question that has be unresolved for a long period of time. To determine the factor having the largest impact of T cell infiltration, candidate neoantigens and self-antigens were identified from TCGA and KCP samples. For RCCs, the expression of the specific experimentally validated HERV-E found by Cherkasova et al was profiled. In each patient sample, each TCR was assigned, detected by Mixcr from the RNA-Seq data, to one of the antigens (neoantigen, self-antigens, or HERV-E) based on the lowest predicted binding ranking. A binding ranking cutoff was also used. Accordingly, to be assigned to an antigen, the binding rank for a particular TCR to at least one antigen must be lower than each one of a series of cutoffs between 0.00% and 2%. In the formed TCR antigen pairs, LUAD, LUSC, and SKCM tumors had more neoantigens than RCC tumors due to the low mutational load of RCCs.

Figure 23:
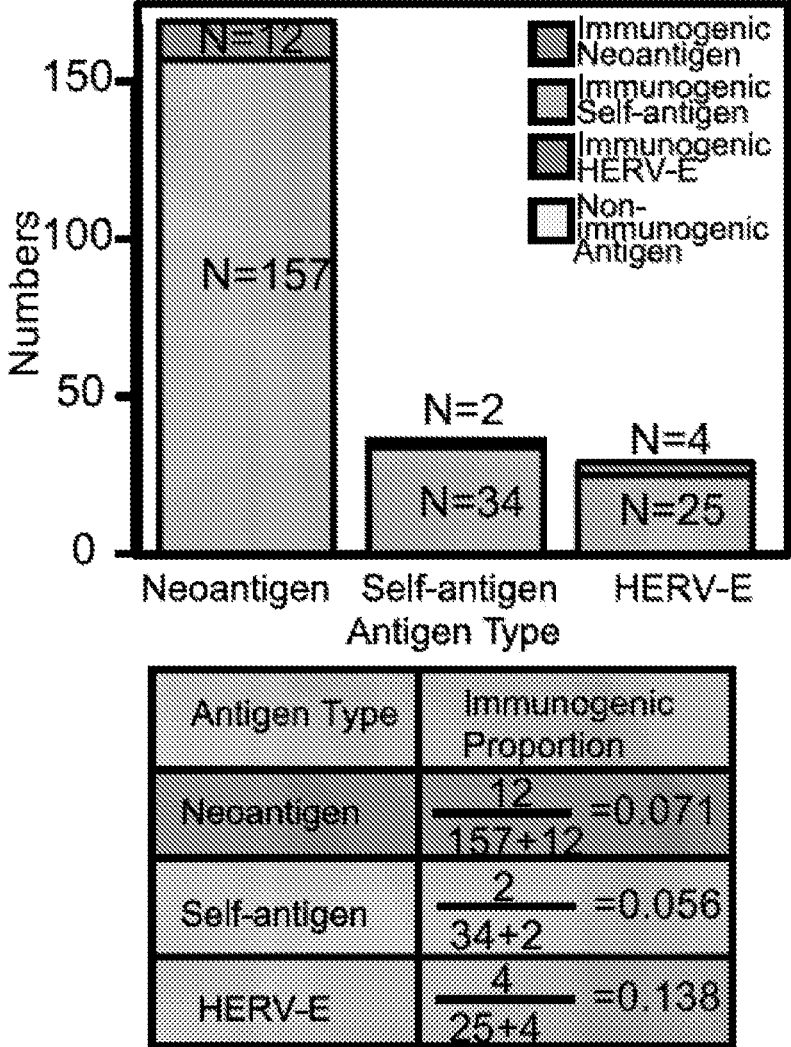
FIG. 23 is a graph illustrating the total and immunogenic antigen numbers for one example patient, according to various embodiments of the present disclosure.
Figure 24:
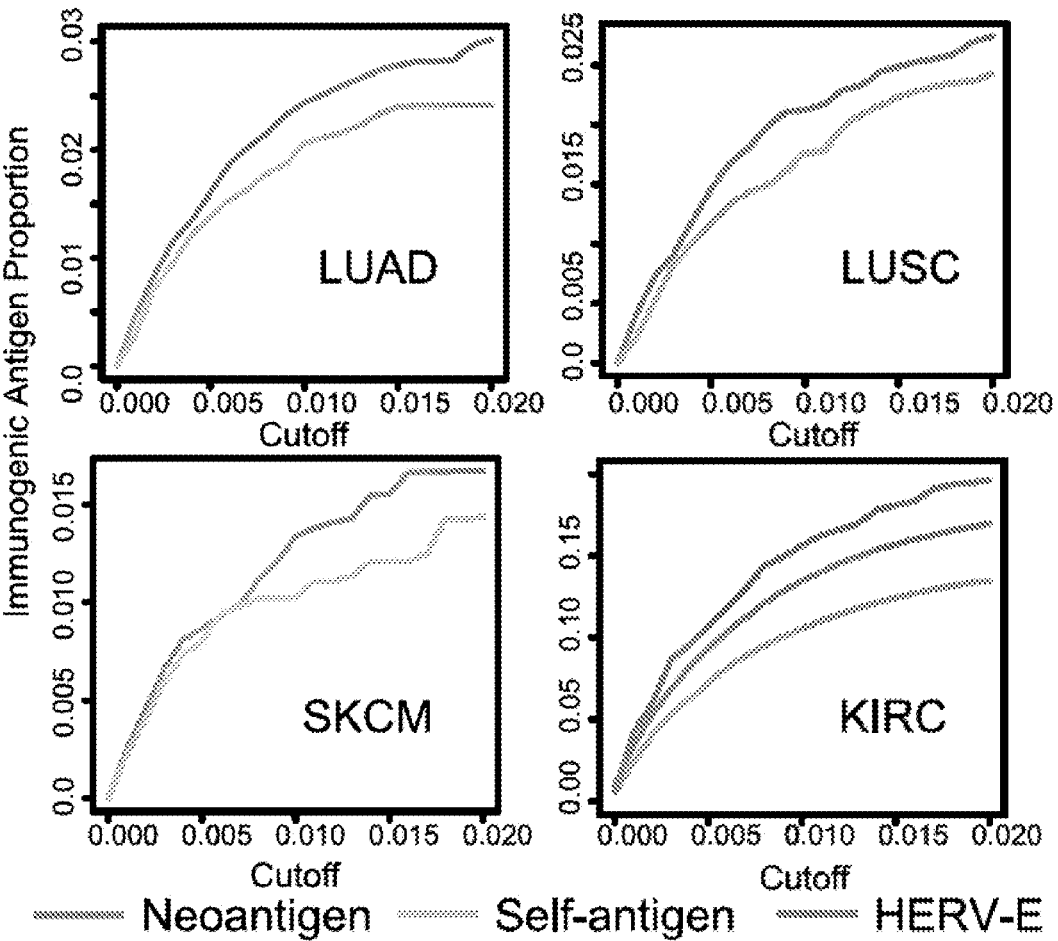
FIG. 24 is a set of graphs illustrating the average immunogenic percentage for neoantigens and self-antigens across four different cancer types, according to various embodiments of the present disclosure.

For each patient sample, the percentage of antigens predicted to bind at least one TCR (defined as immunogenic antigen) was calculated for each class of antigens. FIG. 23 is a graph illustrating the total and immunogenic antigen numbers for one example patient. The proportion of immunogenic antigens for neoantigen, self-antigen, and HERV-E for each patient was calculated and averaged across all patients. FIG. 24 includes for graphs with each graph illustrating the average immunogenic percentage for neoantigens and self-antigens in each of the four cancer types across the total cutoff range. As shown, the average immunogenic percentage was comparable for neoantigens and self-antigens in each of the four cancer types across all cutoffs from 0.00 to 0.02, but neoantigens were always more immunogenic than self-antigens (higher proportions of neoantigens are predicted to bind TCRs). The neoantigens being more immunogenic may be because neoantigens, unlike self-antigens, are mutated peptides that have not been encountered by T cells during the developmental process. For the kidney cancer patient, the HERV antigens were observed to be more likely to be immunogenic than both neoantigens and self-antigens which may indicate the importance of HERV-E in inducing immunity responses in kidney cancers.

Figure 25:
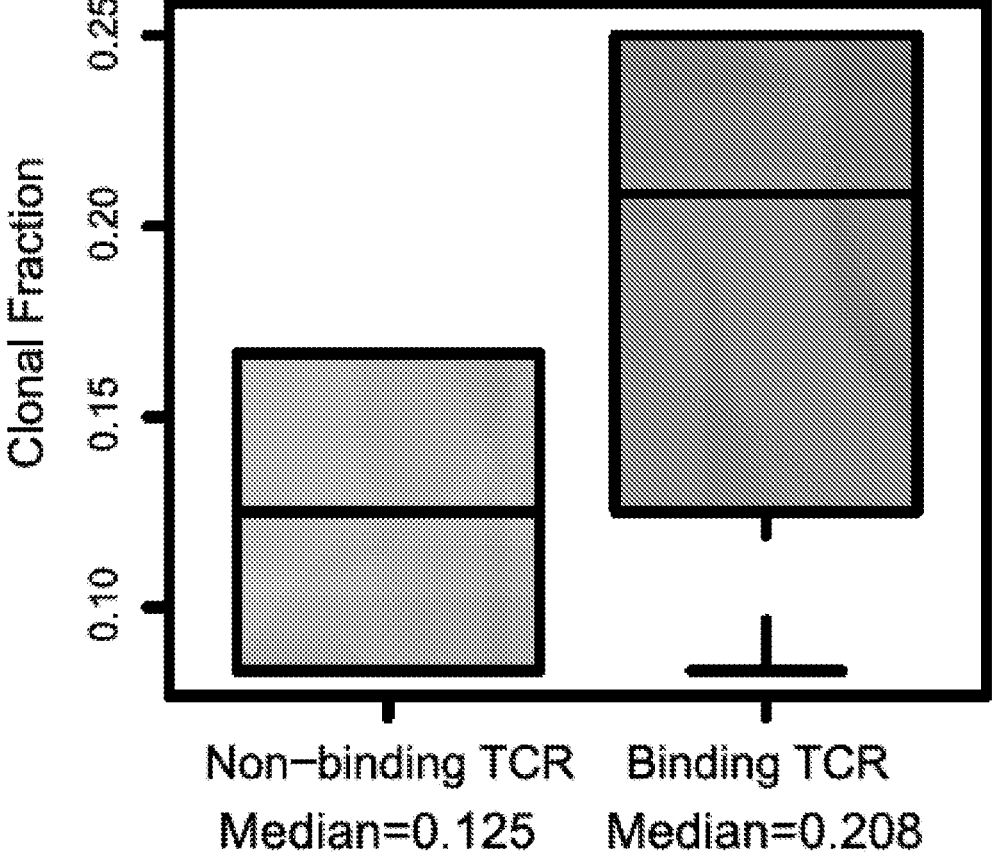
FIG. 25 is a graph illustrating the average clonal fractions for non-binding TCRs and binding TCRs for one example patient, according to various embodiments of the present disclosure.
Figure 26:
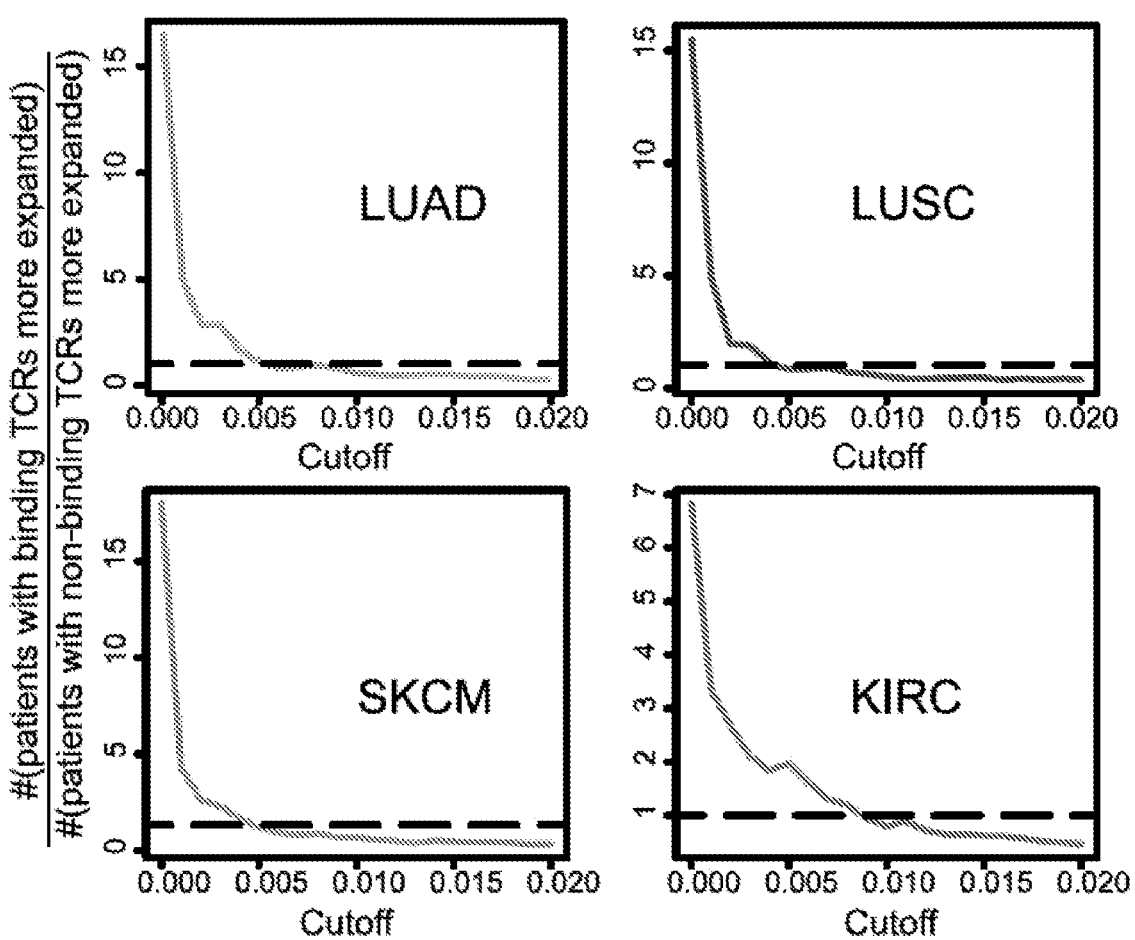
FIG. 26 is a set of graphs illustrating the ratio of patients with binding T cells having a higher average clone size to patients having non-binding T cells having a higher average clone size for different cancer types, according to various embodiments of the present disclosure.

The impact of TCR-pMHC interactions on the clonal expansion of T cells was determined. For each patient, the clonal fractions of TCRs (# specific TCR clonotype/# all TCRs) that were predicted to be binding were compared to any of neoantigens, self-antigens, and HERV antigens, and also the clonal fractions of the other non-binding T cells. FIG. 25 is a graph illustrating the average clonal fractions for non-binding TCRs and binding TCRs for one example patient. As shown, this patient's binding T cells have a higher average clone size than non-binding T cells. For each of the four cancer types, the number of patients with binding T cells having a higher average clone size was calculated and divided by the number of patients with non-binding T cells having a higher average clone size. FIG. 26 includes four graphs with each graph illustrating the ratio of patients with binding T cells having a higher average clone size to patients having non-binding T cells having a higher average clone size for a different cancer type across all of the cutoff stages. As shown, patients are more likely to show the phenotype that the binding T cells are more clonally expanded than non-binding T cells. This result indicates that more immunogenic tumor antigens induce stronger clonal expansions of T cells in human tumors.

Example 6—Impact of TCR-Neoantigen Interactions on Tumor Progression and Immunotherapy Treatment Response The physiological importance of the TCR-pMHC interactions profiled by the machine learning model was also evaluated. Specifically, the TCR-pMHC interactions including tumor neoantigens were analyzed because tumor neoantigens are associated with somatic mutations, which can be directly linked to the fitness of tumor clones. In a given tumor, some neoantigens bind TCRs of T cells that are more clonally expanded and other neoantigens bind T cells that are less expanded. On the other hand, some neoantigens may be from mutations that are truncal (higher variant allele frequency), while other neoantigens may be from subclonal mutations. When the truncal neoantigens bind more clonally expanded TCRs, the distribution of neoantigens and T cells may favor the elimination of tumor cells, which could be beneficial for prognosis and immunotherapy treatment response. To quantitatively measure this effect, a neoantigen immunogenicity effectiveness score (NIES) was developed based on the product of the variant allele frequency (VAF) of the neoantigen's corresponding mutation and the clonal fraction of the TCRs that bind the same neoantigen. Proper normalizations were carried out to remove the confounding effect of tumor purity and the total T cell infiltration. The higher the NIES score is, the more expanded TCRs are concentrated in the truncal neoantigens, which is a more favorable distribution according to our hypothesis.

Figure 27:
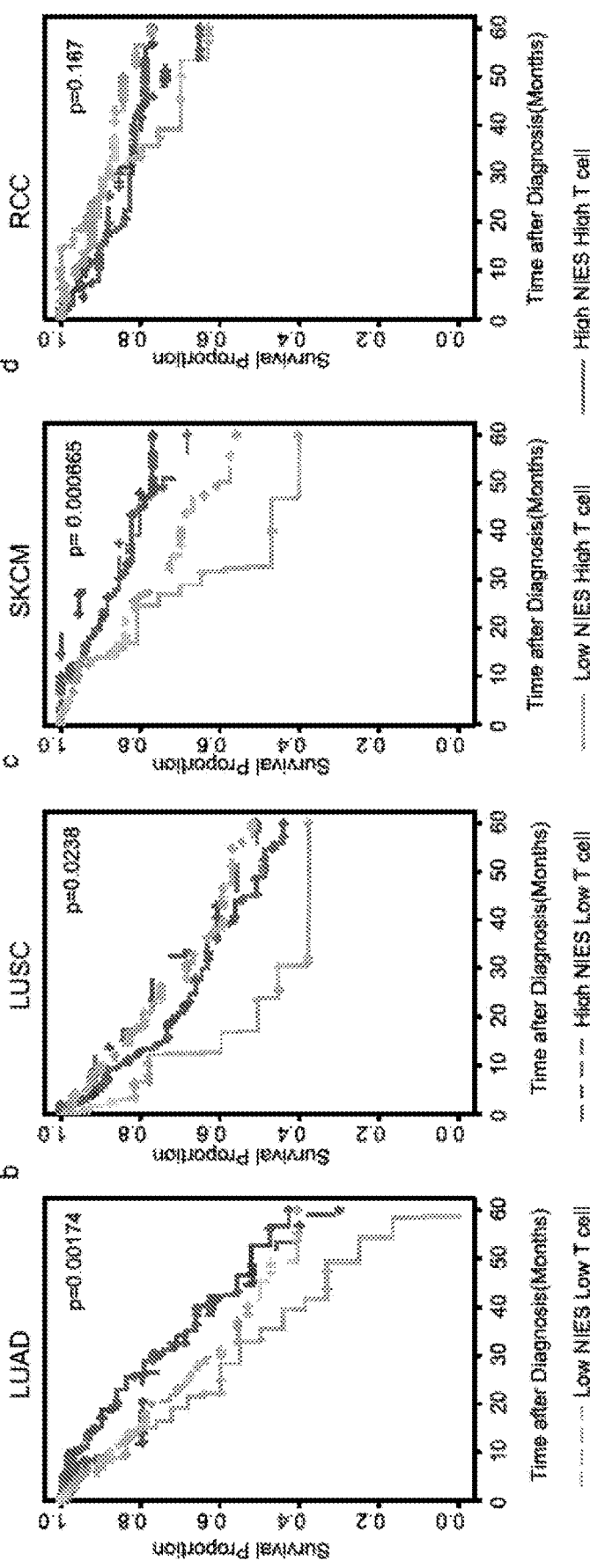
FIG. 27 is a set of graphs illustrating the relationship between neoantigen immunogenicity effectiveness scores (NIES) and survival rates in different lung cancer and melanoma cohorts, according to various embodiments of the present disclosure.
Figure 28:
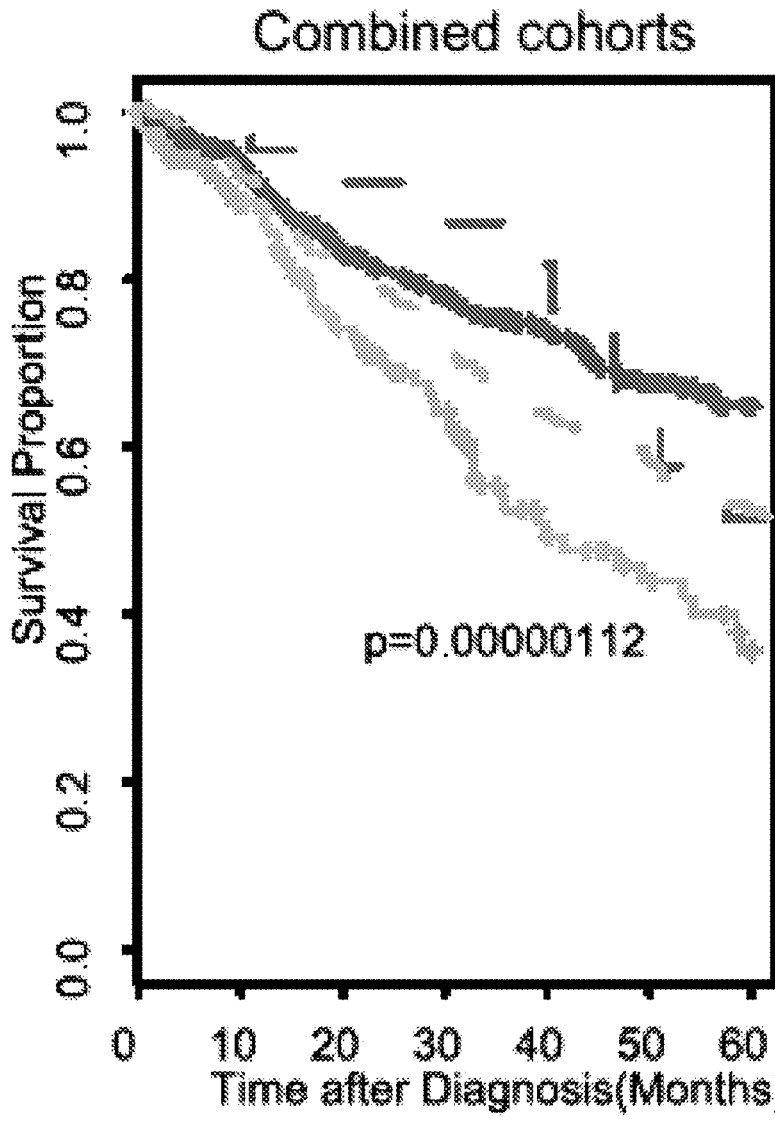
FIG. 28 is a graph illustrating the NIES to survival association for an integrated cohort that combines the lung cancer and melanoma patients with high T cell infiltration, according to various embodiments of the present disclosure.
Figure 29:
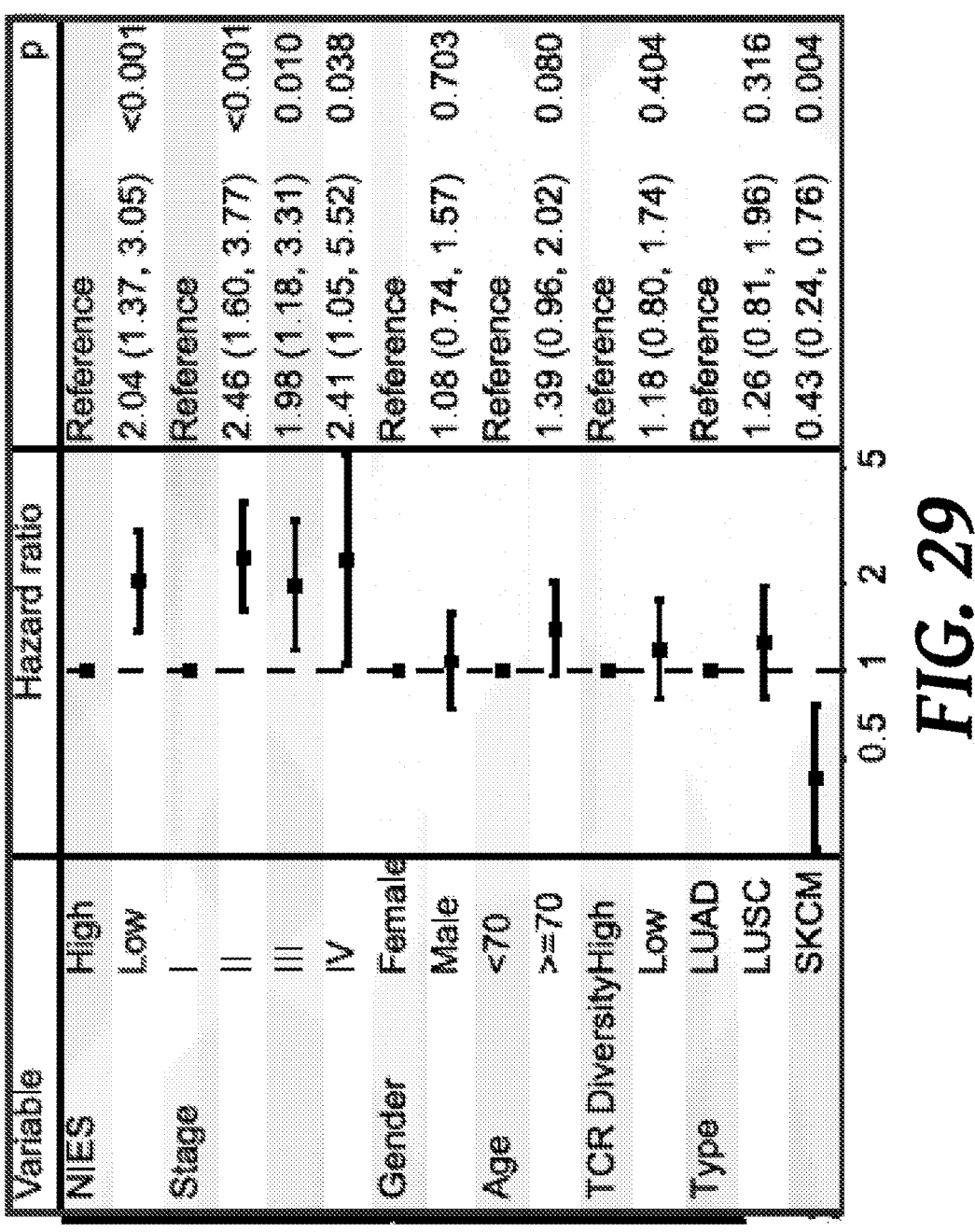
FIG. 29 is a table illustrating the results of the multivariate analysis performed on the integrated cohort, according to various embodiments of the present disclosure.

To validate NIES as a physiologically relevant metric, the association between NIES and prognosis was evaluated in the LUAD, LUSC, SKCM, and RCC (UTSW KCP+TCGA KIRC) cohorts. The patients in each cohort with high levels of total T cell infiltration were analyzed because the neoantigen-T cell axis is more likely to be functionally active when there is sufficient T cell infiltration. FIG. 27 includes four graphs with each graph illustrating the relationship between NIES scores and survival rates in a different lung cancer and melanoma cohorts. As shown, higher NIES scores had a significant association with better survival in the lung cancer and melanoma patients (e.g., the far left graph shows the association for LUAD with a P=0.00174; the graph second from the left shows the association for LUSC with a P=0.0238; and the graph second from the right shows the association for SKCM, with a P=0.000665. Conversely, as shown in the graph on the far right, NIES is not prognostic in kidney cancer (i.e., the RCC cohort). For all four cohorts, the overall survival of patients with low T cell infiltration was indifferent to the levels of NIES. However, the difference between kidney cancer and the other cancer types seems to reflect the unique features of kidney cancers such as low mutational load and reactivation of HERV-E. FIG. 28 is a graph illustrating the NIES to survival association for an integrated cohort that combines the lung cancer and melanoma patients with high T cell infiltration. As shown, the survival analysis of this integrated cohort again shows that patients with higher NIES have a better overall prognosis (P=$1.12 \times 10^{-6}$). A multivariate analysis adjusted by disease type, stage, gender, age, and TCR repertoire diversity was also performed in the combined cohort. TCR repertoire diversity, measured by Shannon's entropy (H) index, is a known biomarker for prognosis assessment. FIG. 29 is a table illustrating the results of the multivariate analysis. As shown, the significant association between survival rate and NIES still held (P<0.001). The analyses shown in FIGS. 28-29 were carried out using a binding ranking cutoff of 1%. Using a series of different cutoffs, we obtained very similar results. FIG. 30 is a table illustrating the results of an analysis of other candidate biomarkers performed on the lung cancer and melanoma cohorts. As a benchmark, patients were dichotomized by the median of neoantigen load, T cell infiltration, or TCR diversity and performed the same analyses. As shown, NIES was much more strongly prognostic than the other candidate biomarkers.

Similarly, the implication of TCR-neoantigen interaction efficiency for treatment response prediction was evaluated. A total of 139 melanoma patients on immune checkpoint inhibitor treatment from Liu et al[5], Van Allen et al[6] and Hugo et al[7] were analyzed. Patients were divided into two groups based on the median of NIES. Patients with high NIES were shown to have better overall survival and vice versa at binding affinity cutoff at 1%. The analysis was repeated using different rank cutoffs (0.1%, 0.5%, 2%) and the relationship between high NIES and better survival were also observed for the different rank cutoffs with statistical significance achieved. A cohort of anti-PD-L1 treated metastatic gastric cancer patients were also analyzed. No survival information was available for this cohort so categorical response evaluation criteria in solid tumors (RECIST) response variables was substituted for survival. The study revealed an overall trend that patients with better responses have higher NIES scores with statistical significance achieved. Results of other binding rank cutoffs replicated these results with statistical significance achieved. For comparison, a cohort of ccRCC patients on anti-PD1/anti-PD-L1 from Miao et al[8] was also analyzed. However, no significant association between NIES and the survival rate of these ccRCC patients was observed. NIES was also benchmarked against total neoantigen load, T cell infiltration, and TCR repertoire diversity to demonstrate the advance of NIES over these three other biomarkers. To systematically assess the significance of these comparisons, the bootstrap technique was leveraged to confirm that the advances are statistically significant.

System Hardware

Figure 31:
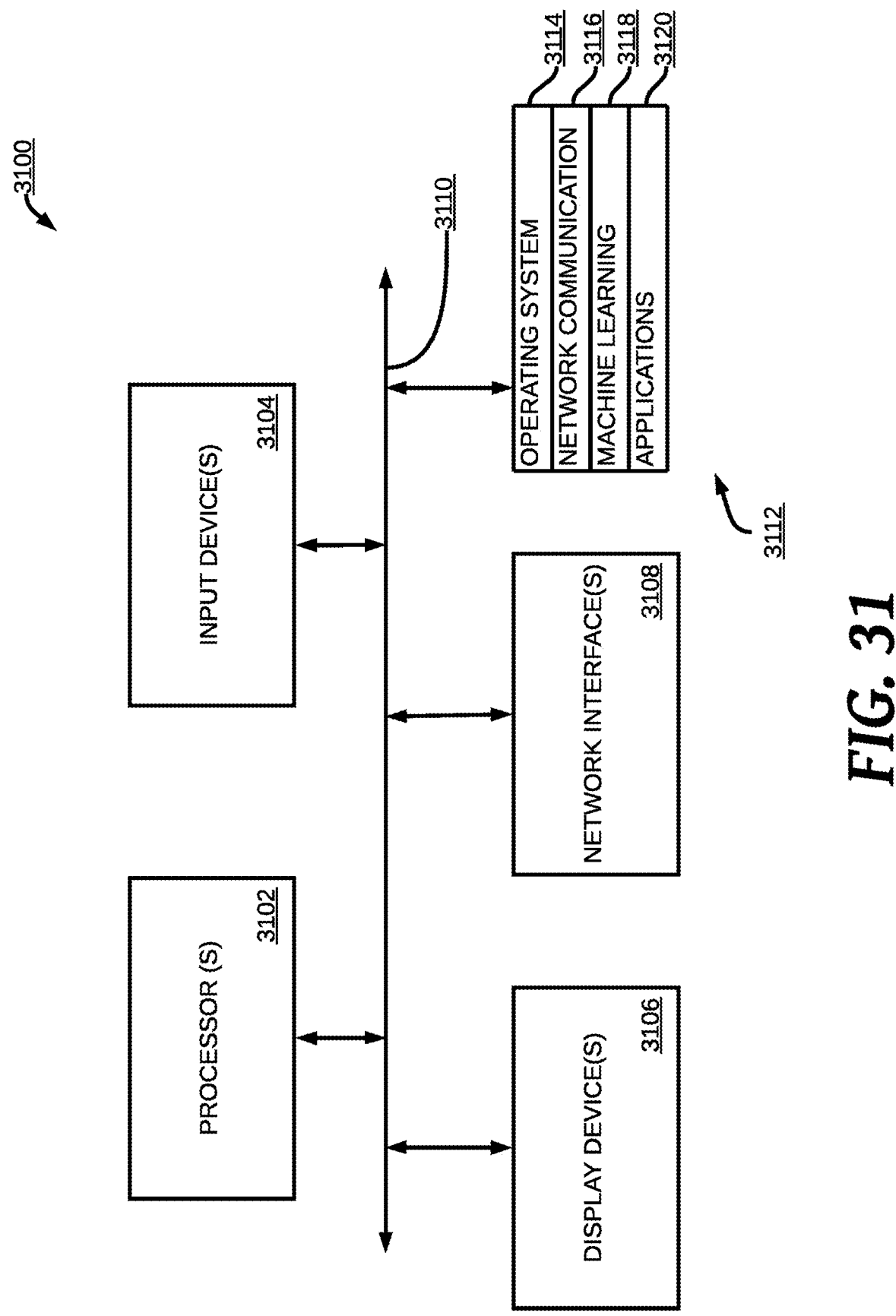
FIG. 31 is a block diagram illustrating an example computing device according to various embodiments of the present disclosure.

FIG. 31 shows an example computing device according to an embodiment of the present disclosure. The computing device 3100 may include a machine learning service that generates binding specificity predictions for TCR-pMHC pairs. The computing device 3100 may be implemented on any electronic device that runs software applications derived from compiled instructions, including without limitation personal computers, servers, smart phones, media players, electronic tablets, game consoles, email devices, etc. In some implementations, the computing device 3100 may include one or more processors 3102, one or more input devices 3104, one or more display devices 3106, one or more network interfaces 3108, and one or more computer-readable mediums 3112. Each of these components may be coupled by bus 3110, and in some embodiments, these components may be distributed among multiple physical locations and coupled by a network.

Display device 3106 may be any known display technology, including but not limited to display devices using Liquid Crystal Display (LCD) or Light Emitting Diode (LED) technology. Processor(s) 3102 may use any known processor technology, including but not limited to graphics processors and multi-core processors. Input device 3104 may be any known input device technology, including but not limited to a keyboard (including a virtual keyboard), mouse, track ball, camera, and touch-sensitive pad or display. Bus 3110 may be any known internal or external bus technology, including but not limited to ISA, EISA, PCI, PCI Express, USB, Serial ATA or FireWire. Computer-readable medium 3112 may be any non-transitory medium that participates in providing instructions to processor(s) 3102 for execution, including without limitation, non-volatile storage media (e.g., optical disks, magnetic disks, flash drives, etc.), or volatile media (e.g., SDRAM, ROM, etc.).

Computer-readable medium 3112 may include various instructions 3114 for implementing an operating system (e.g., Mac OS®, Windows®, Linux). The operating system may be multi-user, multiprocessing, multitasking, multi-threading, real-time, and the like. The operating system may perform basic tasks, including but not limited to: recognizing input from input device 3104; sending output to display device 3106; keeping track of files and directories on computer-readable medium 3112; controlling peripheral devices (e.g., disk drives, printers, etc.) which can be controlled directly or through an I/O controller; and managing traffic on bus 3110. Network communications instructions 3116 may establish and maintain network connections (e.g., software for implementing communication protocols, such as TCP/IP, HTTP, Ethernet, telephony, etc.).

Machine learning instructions 3118 may include instructions that enable computing device 3100 to function as a machine learning service and/or to train machine learning models, train prediction models, determine binding specificity predictions, and the like as described herein. Application(s) 3120 may be an application that uses or implements the processes described herein and/or other processes. The processes may also be implemented in operating system 3114. For example, application 3120 and/or operating system may create tasks in applications as described herein.

The described features may be implemented in one or more computer programs that may be executable on a programmable system including at least one programmable processor coupled to receive data and instructions from, and to transmit data and instructions to, a data storage system, at least one input device, and at least one output device. A computer program is a set of instructions that can be used, directly or indirectly, in a computer to perform a certain activity or bring about a certain result. A computer program may be written in any form of programming language (e.g., Objective-C, Java), including compiled or interpreted languages, and it may be deployed in any form, including as a stand-alone program or as a module, component, subroutine, or other unit suitable for use in a computing environment.

Suitable processors for the execution of a program of instructions may include, by way of example, both general and special purpose microprocessors, and the sole processor or one of multiple processors or cores, of any kind of computer. Generally, a processor may receive instructions and data from a read-only memory or a random access memory or both. The essential elements of a computer may include a processor for executing instructions and one or more memories for storing instructions and data. Generally, a computer may also include, or be operatively coupled to communicate with, one or more mass storage devices for storing data files; such devices include magnetic disks, such as internal hard disks and removable disks; magneto-optical disks; and optical disks. Storage devices suitable for tangibly embodying computer program instructions and data may include all forms of non-volatile memory, including by way of example semiconductor memory devices, such as EPROM, EEPROM, and flash memory devices; magnetic disks such as internal hard disks and removable disks; magneto-optical disks; and CD-ROM and DVD-ROM disks.

The processor and the memory may be supplemented by, or incorporated in, ASICs (application-specific integrated circuits).

To provide for interaction with a user, the features may be implemented on a computer having a display device such as an LED or LCD monitor for displaying information to the user and a keyboard and a pointing device such as a mouse or a trackball by which the user can provide input to the computer.

The features may be implemented in a computer system that includes a back-end component, such as a data server, or that includes a middleware component, such as an application server or an Internet server, or that includes a front-end component, such as a client computer having a graphical user interface or an Internet browser, or any combination thereof. The components of the system may be connected by any form or medium of digital data communication such as a communication network. Examples of communication networks include, e.g., a telephone network, a LAN, a WAN, and the computers and networks forming the Internet.

The computer system may include clients and servers. A client and server may generally be remote from each other and may typically interact through a network. The relationship of client and server may arise by virtue of computer programs running on the respective computers and having a client-server relationship to each other.

One or more features or steps of the disclosed embodiments may be implemented using an API. An API may define one or more parameters that are passed between a calling application and other software code (e.g., an operating system, library routine, function) that provides a service, that provides data, or that performs an operation or a computation.

The API may be implemented as one or more calls in program code that send or receive one or more parameters through a parameter list or other structure based on a call convention defined in an API specification document. A parameter may be a constant, a key, a data structure, an object, an object class, a variable, a data type, a pointer, an array, a list, or another call. API calls and parameters may be implemented in any programming language. The programming language may define the vocabulary and calling convention that a programmer will employ to access functions supporting the API.

In some implementations, an API call may report to an application the capabilities of a device running the application, such as input capability, output capability, processing capability, power capability, communications capability, etc.

While various embodiments have been described above, it should be understood that they have been presented by way of example and not limitation. It will be apparent to persons skilled in the relevant art(s) that various changes in form and detail can be made therein without departing from the spirit and scope. In fact, after reading the above description, it will be apparent to one skilled in the relevant art(s) how to implement alternative embodiments. For example, other steps may be provided, or steps may be eliminated, from the described flows, and other components may be added to, or removed from, the described systems. Accordingly, other implementations are within the scope of the following claims.

In addition, it should be understood that any figures which highlight the functionality and advantages are presented for example purposes only. The disclosed methodology and system are each sufficiently flexible and configurable such that they may be utilized in ways other than that shown.

Although the term "at least one" may often be used in the specification, claims and drawings, the terms "a", "an", "the", "said", etc. also signify "at least one" or "the at least one" in the specification, claims and drawings.

Finally, it is the applicant's intent that only claims that include the express language "means for" or "step for" be interpreted under 35 U.S.C. 112(f). Claims that do not expressly include the phrase "means for" or "step for" are not to be interpreted under 35 U.S.C. 112(f).

REFERENCES

1. Liu, Y. C. et al. Highly divergent T-cell receptor binding modes underlie specific recognition of a bulged viral peptide bound to a human leukocyte antigen class I molecule. *J. Biol. Chem.* 288, 15442-15454 (2013).

2. Cole, D. K. et al. T-cell receptor (TCR)-peptide specificity overrides affinity-enhancing TCR-major histocompatibility complex interactions. *J. Biol. Chem.* 289, 628-638 (2014).

3. Valkenburg, S. A. et al. Molecular basis for universal HLA-A*0201-restricted CD8+ T-cell immunity against influenza viruses. *Proc Natl Acad Sci USA* 113, 4440-4445 (2016).

4. Cherkasova, E. et al. Detection of an Immunogenic HERV-E Envelope with Selective Expression in Clear Cell Kidney Cancer. *Cancer Res.* 76, 2177-2185 (2016).

5. Liu, D. et al. Integrative molecular and clinical modeling of clinical outcomes to PD1 blockade in patients with metastatic melanoma. *Nat. Med.* 25, 1916-1927 (2019).

6. Van Allen, E. M. et al. Genomic correlates of response to CTLA-4 blockade in metastatic melanoma. *Science* 350, 207-211 (2015).

7. Hugo, W. et al. Genomic and Transcriptomic Features of Response to Anti-PD-1 Therapy in Metastatic Melanoma. *Cell* 165, 35-44 (2016).

8. Miao, D. et al. Genomic correlates of response to immune checkpoint therapies in clear cell renal cell carcinoma. *Science* 359, 801-806 (2018).

The invention claimed is:

1. A method of predicting T cell receptor (TCR) binding specificities comprising:
   determining a set of MHC embeddings that encode neoantigen and major histocompatibility complex (MHC) data for a plurality of MHC proteins (pMHC);
   determining a set of TCR embeddings that encode TCR data for a plurality of TCR sequences;
   pre-training a prediction model on the set of MHC embeddings and the set of TCR embeddings;
   training the prediction model using a differential learning schema that feeds a binding TCR-pMHC pair and a non-binding TCR-pMHC pair into the prediction model during each training cycle; and
   determining a prediction for binding specificity of an input TCR-pMHC pair based on the prediction model.

2. The method of claim 1, further comprising:
   obtaining a set of TCR-pMHC pairs that are experimentally validated as immunogenic, the set of TCR-pMHC pairs including the input TCR-pMHC pair; and
   validating the prediction model by comparing the binding specificity prediction for the input TCR-pMHC pair to a known binding specificity for the input TCR-pMHC pair.

3. The method of claim 1, further comprising:
   determining a clonal expansion of a plurality of T cells, the clonal expansion including multiple TCR clones having known binding interactions with a set of pMHCs and a clone size for each of the multiple TCR clones;

determining a prediction for binding specificity between each of the multiple TCR clones and each of the pMHCs included in the set of pMHCs based on the prediction model; and validating the prediction model by comparing the clone size for each of the TCR clones to the predicted binding specificity.

4. The method of claim 1, wherein each of the MHC embeddings includes a numeric representation of one or more pMHCs, and the method further comprising:

training a MHC numeric embedding layer on a MHC training dataset including textual representations of pMHCs; and determining the numeric representation of the one or more pMHCs for each of the MHC embeddings based on the MHC numeric embedding layer.

5. The method of claim 1, wherein the MHC embeddings are determined using a multi-layer neural network that determines a probability that a particular pMHC molecule binds to one or more neo-antigen protein sequences.

6. The method of claim 1, wherein each of the TCR embeddings include a numeric representation of one or more TCR protein sequences, and the method further comprising:

training a TCR numeric embedding layer on a TCR training dataset including multiple training TCR protein sequences, the TCR training dataset including a structured data representation of one or more biochemical properties of multiple amino acids included in the training TCR protein sequences; and determining the numeric representation of the one or more TCR protein sequences based on the TCR numeric embedding layer.

7. The method of claim 6, wherein the multiple amino acids are included in a complementary determining region (CDR) of the training TCR protein sequences, and the method further comprising:

manipulating the structured data representation to enable amino acids from multiple CDRs of the training TCR protein sequences to be added to the TCR training dataset.

8. The method of claim 1, wherein the TCR embeddings are determined using an auto-encoder that includes multiple encoder layers and multiple decoder layers.

9. The method of claim 1, further comprising normalizing the MHC embeddings and the TCR embeddings to enable the prediction model to be pre-trained on multiple classes of pMHCs.

10. The method of claim 1, wherein the prediction for binding specificity includes a variable that describes a percentile rank of a predicted binding strength between the input TCR-pMHC pair, with respect to a background distribution including the predicted binding strength between each TCR included in a pool of 10,000 randomly sampled TCRs and a pMHC included in the input TCR-pMHC pair.

11. A system for predicting T cell receptor (TCR) binding specificities comprising:

a memory including executable instructions; and a processor configured to execute the executable instructions and cause the system to:

determine a set of MHC embeddings that encode neoantigen and major histocompatibility complex (MHC) data for a plurality of MHC proteins (pMHC);

determine a set of TCR embeddings that encode TCR data for a plurality of TCR sequences;

pre-train a prediction model on the set of MHC embeddings and the set of TCR embeddings;

train the prediction model using a differential learning schema that feeds a binding TCR-pMHC pair and a non-binding TCR-pMHC pair into the prediction model during each training cycle; and determine a prediction for binding specificity of an input TCR-pMHC pair based on the prediction model.

12. The system of claim 11, wherein the processor is further configured to:

obtain a set of TCR-pMHC pairs that are experimentally validated as immunogenic, the set of TCR-pMHC pairs including the input TCR-pMHC pair; and validate the prediction model by comparing the binding specificity prediction for the input TCR-pMHC pair to a known binding specificity for the input TCR-pMHC pair.

13. The system of claim 11, wherein the processor is further configured to:

determine a clonal expansion of a plurality of T cells, the clonal expansion including multiple TCR clones having known binding interactions with a set of pMHCs and a clone size for each of the multiple TCR clones;

determine a prediction for binding specificity between each of the multiple TCR clones and each of the pMHCs included in the set of pMHCs based on the prediction model; and validate the prediction model by comparing the clone size for each of the TCR clones to the predicted binding specificity.

14. The system of claim 11, wherein each of the MHC embeddings includes a numeric representation of one or more pMHCs, and the processor is further configured to:

train a MHC numeric embedding layer on a MHC training dataset including textual representations of pMHCs; and determine the numeric representation of the one or more pMHCs for each of the MHC embeddings based on the MHC numeric embedding layer.

15. The system of claim 11, wherein the MHC embeddings are determined using a multi-layer neural network that determines a probability that a particular pMHC molecule binds to one or more neo-antigen protein sequences.

16. The system of claim 11, wherein each of the TCR embeddings include a numeric representation of one or more TCR protein sequences, and the processor is further configured to:

train a TCR numeric embedding layer on a TCR training dataset including multiple training TCR protein sequences, the TCR training dataset including a structured data representation of one or more biochemical properties of multiple amino acids included in the training TCR protein sequences; and determine the numeric representation of the one or more TCR protein sequences based on the TCR numeric embedding layer.

17. The system of claim 16, wherein the multiple amino acids are included in a complementary determining region (CDR) of the training TCR protein sequences, and the processor is further configured to:

manipulate the structured data representation to enable amino acids from multiple CDRs of the training TCR protein sequences to be added to the TCR training dataset.

18. The system of claim 11, wherein the TCR embeddings are determined using an auto-encoder that includes multiple encoder layers and multiple decoder layers.

19. The system of claim 11, wherein the processor is further configured to normalize the MHC embeddings and the TCR embeddings to enable the prediction model to be pre-trained on multiple classes of pMHC.

20. The system of claim 11, wherein the prediction for binding specificity includes a variable that describes a percentile rank of a predicted binding strength between the input TCR-pMHC pair, with respect to a background distribution including the predicted binding strength between each TCR included in a pool of 10,000 randomly sampled TCRs and a pMHC included in the input TCR-pMHC pair.

\* \* \* \* \*